(12) United States Patent
Lu et al.

(10) Patent No.: US 8,462,334 B2
(45) Date of Patent: Jun. 11, 2013

(54) SENSOR SYSTEM WITH PLASMONIC NANO-ANTENNA ARRAY

(76) Inventors: Weixing Lu, Los Angeles, CA (US); Allan Roberts, Buena Park, CA (US)

( * ) Notice: Subject to any disclaimer, the term of this patent is extended or adjusted under 35 U.S.C. 154(b) by 90 days.

(21) Appl. No.: 13/214,176

(22) Filed: Aug. 20, 2011

(65) Prior Publication Data

US 2012/0050732 A1    Mar. 1, 2012

Related U.S. Application Data

(60) Provisional application No. 61/377,082, filed on Aug. 25, 2010.

(51) Int. Cl.
*G01J 3/44* (2006.01)
(52) U.S. Cl.
USPC .......................................................... 356/301
(58) Field of Classification Search
USPC ........ 356/301, 72–73; 977/954, 890; 427/205
See application file for complete search history.

(56) References Cited

U.S. PATENT DOCUMENTS

| 7,206,488 | B1 | 4/2007 | Altug |
| 7,573,045 | B2 | 8/2009 | Gorrell et al. |
| 2008/0083881 | A1* | 4/2008 | Gorrell et al. ................. 250/399 |
| 2010/0110424 | A1 | 5/2010 | Wang |
| 2010/0129623 | A1 | 5/2010 | Johansson et al. |

* cited by examiner

*Primary Examiner* — Tarifur Chowdhury
*Assistant Examiner* — Abdullahi Nur
(74) *Attorney, Agent, or Firm* — Jerome E. Sacks

(57) ABSTRACT

In order to provide the high sensitivity SERS active substrates needed for rapid and sensitive chemical/biological agent detection, the present invention provides a Plasmonic Nano-antenna Array (PNA) substrate with large local electromagnetic field enhancements; a controllable and repeatable nano-fabrication process for creating the PNA surface; and a system design for a compact, portable device capable of using the PNA technology to acquire and analyze target molecular samples. Both 2D and 3D systems are provided.

18 Claims, 26 Drawing Sheets

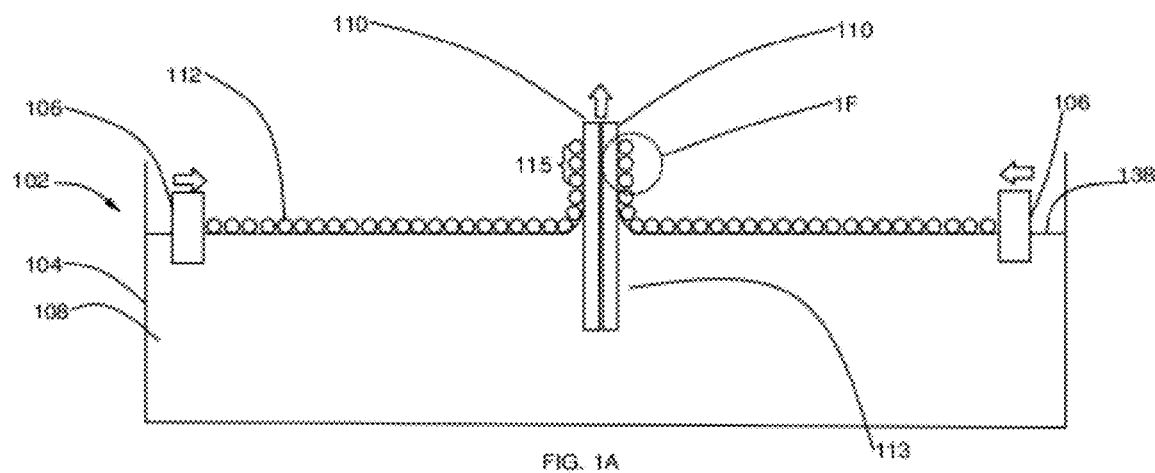

| | Mask alignment process | Self-assembly process to modify substrate surface | LBCSA process to fabricate PNA pattern on glass |
|---|---|---|---|
| I Fabricate PNA array with gold particle diameter $D_1$ and dimer gap $d_1$. | 1 | 2 | 3 |
| II Fabricate PNA array with gold particle diameter $D_2$ and dimer gap $d_2$. | 4 | 5 | 6 |
| III Fabricate PNA array with gold particle diameter $D_3$ and dimer gap $d_3$. | 7 | 8 | 9 |
| IV Fabricate PNA array with gold particle diameter $D_4$ and dimer gap $d_4$. | 10 | 11 | 12 |

FIG. 4

SENSOR SYSTEM WITH PLASMONIC NANO-ANTENNA ARRAY

CROSS-REFERENCE TO RELATED APPLICATIONS

This application claims the benefit of the U.S. Provisional Patent Application No. 61/377,082 filed Aug. 25, 2010 by the present inventors. This provisional patent application is incorporated herein in its entirety by reference.

TECHNICAL FIELD

The present invention relates generally to creating a specific nano-structure on a substrate to improve the sensitivity of surface enhanced Raman spectroscopy (SERS).

BACKGROUND OF THE DISCLOSURE

Certain chemical and biological contaminants can be harmful or dangerous at very low levels (low parts per billion (ppb) for chemicals and 1-100 cts/ml for biological agents) and, therefore, a rapid and sensitive detection of such toxins and pollutants in air and drinking water, followed by rapid remediation, is critically important. However, many biological and chemical materials such as explosives, protein biotoxins and some microbial materials cannot be detected by current methods such as binding affinity or fluorescent assays.

On the other hand, Raman spectroscopy holds potential for a wide variety of high resolution sensing of molecular compounds in air and water for environmental protection applications. This technique measures the photon energy of scattering monochromatic light reflected when a laser illuminates target molecules. The measured shifts in photon energy provide information for molecular identification. For example, many molecules/materials of interest exhibit unique Raman spectra that can be used as fingerprints for direct molecular/material identification[1, 2].

Raman spectroscopy, however, suffers from its very weak signal strength, especially for portable Raman spectroscopy systems. In fact, the Raman scattering cross section of molecules is about 10-12 orders of magnitude smaller than the fluorescent scattering cross section of laser dyes. However, since the discovery of significant enhancements of Raman scattering using metallic surfaces or nanostructures, surface enhanced Raman spectroscopy (SERS) has been explored in different fields. Importantly, recent experimental observations have shown that in certain situations, SERS enhancements can improve signals strength by as much as $10^{14} \sim 10^{15}$ times, elevating SERS to single molecule sensing levels[3-7]. This great potential of SERS can best be realized in conjunction with new plasmonic nanostructures that can not only provide extraordinary local field enhancements, but can also be fabricated via a controllable, reproducible, large scale process.

Studies have shown that large field enhancements are usually localized at the nano-gaps of nano-antennas and the enhancements improve dramatically when the gap size decreases below 5 nm[5, 8]. These studies are based on single molecule SERS experiments that typically use aggregates of colloidal nanoparticles where the "hot-spots" of enhanced local fields are obtained only by chance and are not controllable[3-7]. The particular challenge to achieving repeatable and controllable SERS active substrates originates from the difficulty of fabricating large-scale arrays of nano-gaps in a controllable and repeatable manner. The existing approaches employ MEMS fabrication processes that are extremely expensive and make these approaches non-cost-effective.

Recent studies in plasmonics, however, have led to a better understanding of surface plasmon resonance and local field enhancements that hold promise for novel designs and large-scale fabrication of single molecule SERS active substrates. For example, a variety of designs of optical nano-antennas have been proposed and demonstrated. Particularly, by varying the geometric parameters of the plasmonic nano-antennas, local field enhancements and plasmon resonance can be fine tuned[9-11]. Moreover, by confining molecules within the nano-gap between two metal electrodes, SERS and molecular electronic measurements are combined[12, 13]. Using these redundant sensing mechanisms, false positive sensor readings can essentially be eliminated.

RELATED WORK BY OTHERS: Professor Xiang Zhang's group[11] at the University of California, Berkeley developed plasmon resonance of Au/SiO2 multilayered nanodisks that exhibit several distinctive properties including significantly enhanced plasmon resonances and tunable resonance wavelengths which are tailored to desired values by simply varying dielectric layer thickness while the particle diameter is kept constant. This approach leads to higher scattering intensity and more "hot spots," or regions of strong field enhancement. The multilayered nanodisks were prepared on quartz substrates by electron beam lithography, and electron beam evaporation followed by the standard lift-off process.

Hatice Altug's group at Boston University[17] demonstrated significantly longer plasmon lifetimes and stronger near-field enhancements by embedding the nano-antenna arrays into the substrate. This approach offers a more homogeneous dielectric background allowing stronger diffractive couplings among plasmonic particles leading to strong suppression of the radiative damping and is based on single layer e-beam lithography, reactive ion etching (RIE) and a following lift-off process.

BjÖrn M. Reinhard, et al.[18] fabricated nanoparticle cluster arrays with total lateral dimensions of up to 25.4 μm×25.4 μm on top of a 10 nm thin gold film using template-guided self-assembly. This approach provides precise control of the structural parameters in the arrays, allowing a systematic variation of the average number of nanoparticles in the clusters (n) and the edge-to-edge separation (Λ) between $1<n<20$ and 50 nm$<Λ<1000$ nm, respectively. Electron beam lithography and lift-off process are used to define binding sites on which the dielectrically coated nanoparticles self-assemble.

The above approaches for fabrication of plasmonic nano-antenna arrays require very expensive processes such as electron beam lithography, and electron beam evaporation and lift-off processes. These processes are limited to fabricating micron scale arrays that are not scalable to the desired commercial applications of the preferred embodiment of the present invention.

Professor P. Van Duyne's group at Northwestern University[16] developed an inexpensive, simple to implement, inherently parallel, high throughput, nanofabrication technique capable of producing an unexpectedly large variety of nanoparticle structures and well-ordered 2D nanoparticle arrays. The process involves drop coating polymer nanospheres onto a substrate and then allowing the nanospheres to self-assemble into a close-packed hexagonal array. The array is then used as a mask for the creation of several different SERS active substrates. However, this approach suffers from non-scalability and is uncontrollable because the nanoparticle array is based on evaporation of a solvent from a single droplet resulting in an uncontrollable close-packed hexagonal structure.

SUMMARY OF THE DISCLOSURE

In order to provide the high sensitivity SERS active substrates needed for rapid and sensitive chemical/biological agent detection, the preferred embodiment of the present invention provides (1) a Plasmonic Nano-antenna Array (PNA) substrate with large local electromagnetic field enhancements; (2) a controllable and repeatable nano-fabrication process for creating the PNA surface; and (3) a system design for a compact, portable device capable of using the PNA technology to acquire and analyze target molecular samples.

The first embodiment of the present invention represents a key advance in the important field of Raman spectroscopy and nano-structure fabrication and will lead not only to greatly increased chemical detection capabilities but also to numerous new products to address a wide range of physical, chemical, medical and environmental sensor applications. The first embodiment of the present invention improves Raman sensor performance by constructing and applying a new type of substrate to the Raman sensor that possesses the required surface nano-architecture. The first embodiment also includes a low-cost method for nano-fabrication of the required substrates that is highly controllable, scalable, repeatable and low-cost. A first embodiment of the present invention will enable others to pursue the fabrication of nano-structures for many useful applications, such as super lenses, negative refractive index materials, meta-materials, plasmonic devices, enhanced optical transmitters, and equipment for plasmonic nano-lithography. An embodiment of the present invention has the potential to open up new sensor applications with corresponding new markets for U.S. industry.

INNOVATIONS OF THE PNA GAS SAMPLING SYSTEM: The technology has the following advantages over prior approaches:

Ultra-sensitivity: The innovative nano-antenna array based SERS active substrate significantly enhances signal strength by as much as $10^{14}$~$10^{15}$ times, elevating the system to single molecule sensing levels.

High resolution: The technology can not only detect the molecular concentration profile from the VOCs sample mixture, but also can detect and finely resolve the target molecular conformation spectrum profile that specifically relates to the vibration modes of its chemical bonds.

High reliability: The identification mechanism of the technology is based on fingerprints of target molecular conformation structures, by which false positive sensor readings can essentially be eliminated. The confidence of molecular identification also can be enhanced by the innovative sample collection mode (suck-in/adsorption/blow-out Fast: The system can detect, identify and analyze the target molecules from a mixture of gas samples in real-time.

Compact: The system is a compact fiber optical-based system and the size of the entire system can be less than 10 cm×20 cm×30 cm.

Diversity: The system can be used as a powerful gas sensor system and adaptable for any equipment that needs a high resolution and real-time sensor system. The system can also serve as a chemical component analysis system for bio-medical, chemical engineering, and material science research applications.

These advantages are made possible by the following innovations:

Fabrication and incorporation of a nano-antenna array based SERS active substrate Application of a fiber optic-based Raman-Scattering gas sensor system equipped with a operational system software and data base;

Integration of an innovative sample collection device with a suck-in/adsorption/blow-out operation mode.

BRIEF DESCRIPTION OF THE DRAWINGS

FIG. 1A illustrates a two-trough Langmuir-Blodgett trough system.

FIG. 4 illustrates a process based on the PNA technology to fabricate a matrix pattern for multiple excitation purpose.

FIG. 6B illustrates the components of the Ramen instrument including air suction system, diode laser system, and spectrometer system.

PARTS NUMERALS

Figure 1B:
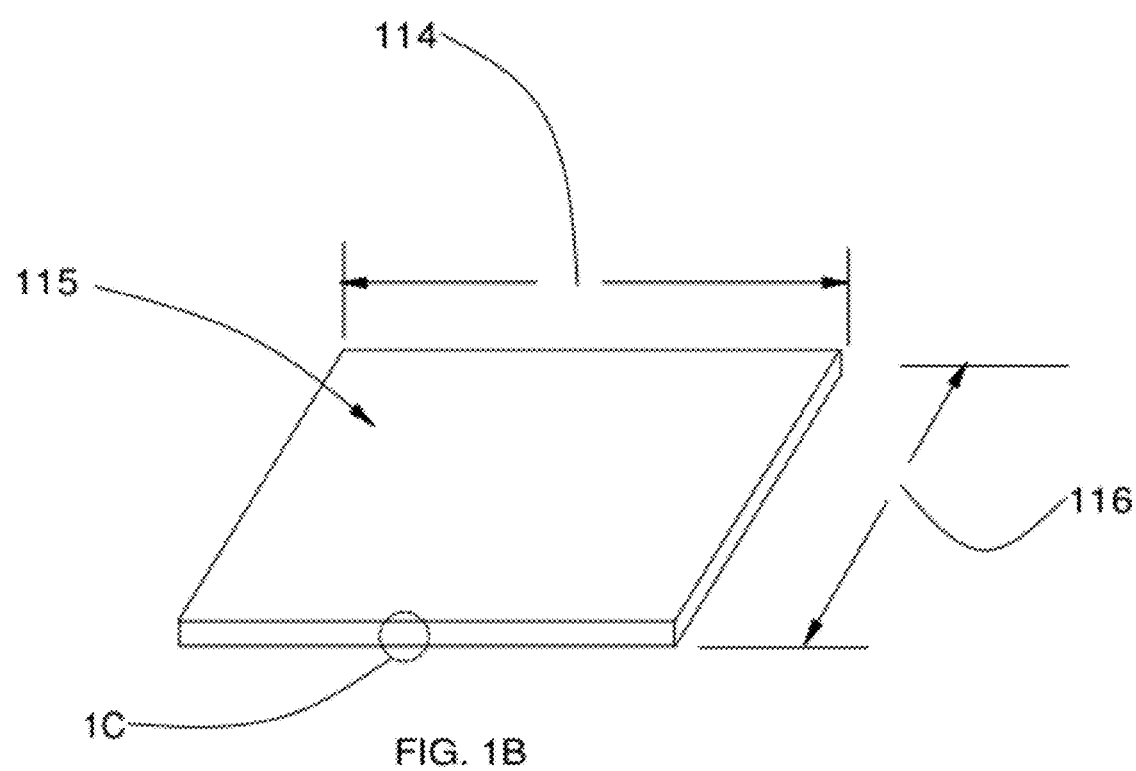
FIG. 1B illustrates a crystal-like nanoparticle array on a solid substrate.

102—water-filled Langmuir-Blodgett trough system
106—barrier
110—glass substrate
110—solid substrate
111—nano-antenna array substrate
112—nanoparticles
113—solid substrate surface
115—nanoparticle array 118—nano-gaps
118—dimer gap
122—incident light
124—target molecule
125—air vacuum pump
126—raman signals
128—nearest neighbor particles pairs
129—nearest neighbor particles pairs
130—amphiphilic molecules
131—plasmonic nano-antenna
132—length
133—pretreated glass surface
133—thiol-terminated glass surface
134—particle size
136—capped nanoparticles
138—water/air interface
140—step motor
142—control box
144—dipping device
146—microbalance
148—mps
150—self-assembly monolayer
152—surface pressure sensor
154—fabricated matrix pattern
156—matrix pattern detailed view
158—size
160—diode laser
162—insert
162 miniature spectrometer
164—sample collection system
164 screen
166—diode laser system
168—air suction system
170—spectrometer system
172—predesigned fiber optical gas sensor head
174—sensor head
176—noble metal nanoparticle detail
178—optical fiber based sensor head
180—working mode
182—air flow channel
188—nano-antenna array
189—ramen apparatus
190—gas flow channels
191—optical minor
192—stainless steel frame
194—plasmonic nano antenna fiber optic bundle
196—optical minors
198—optical lenses
200—filters
202—optical fiber bundle
204—nano-antenna fiber optic bundle array

DETAILED DESCRIPTION

THE PLASMONIC NANO-ANTENNA 131 ARRAY (PNA) SUBSTRATE: FIGS. 1A through 1F schematically illustrate the basic process (FIG. 1A) and resulting plasmonic nano-antennae array structure (FIGS. 1B through 1F) of a first embodiment of nano-antenna array substrate 111 produced by the water-filled Langmuir-Blodgett trough system 102. Such large-scale, highly SERS-active substrates can only be obtained by assembling a crystal-like nanoparticle array 115 on a solid substrate 110 such as glass, metal, acrylic, plastic, optical fiber core, or textile using a Langmuir-Blodgett Controlled Self-Assembly (LBCSA) fabrication technology. The nanoparticles are selected from gold (Au), Silver (Ag), Rhodium (Rh), Palladium (Pd), Osmium (Os), Iridium (Ir), Platinum (Pt), Titanium (Ti) or Aluminum (Al), or a combination of them. In the following, a two-trough Langmuir-Blodgett trough system is described, however the inventive concepts apply to single trough system also.

Again referring to FIGS. 1A through 1F, using this technology, a crystal-like nanoparticle array 115 (see FIG. 1A) can be manipulated and deposited on a solid substrate 110, and the nano-gap 118 between the nearest neighbor particles pairs 128, 129 is precisely controlled at the nanometer level (<5 nm), thereby rendering these particle pairs (dimers) as plasmonic nano-antennas 131 with large local field enhancement. The solid substrate surface 113 of the large scale substrate (up to 10 cm$^2$) is covered with these plasmonic nano-antennas 131 in the form of a close, compact array (FIGS. 1B, 1C), which creates a correspondingly close-packed "hot spot" array covering the solid substrate surface 113 (FIG. 1B). Any target molecule 124 loaded on the SERS active surface arrives at one of the "hot spots" 131 for high SERS enhancement because the close-packed "hot spot" nanoparticle array 115 covers the entire SERS surface. Therefore, the technology creates a new class of active plasmonic nanostructures which are highly effective for SERS-based sensing and that possess the scalability and reproducibility characteristics required for realizing large sensor arrays with extremely uniform properties. The PNA technology not only addresses single-wavelength operation within the nano-antenna array substrate 111, but also addresses the design considerations required for operation at alternative Ramon scattering laser light frequencies that is able to utilize multiple types of lasers and other excitation sources. The nano-antenna array substrate 111 is structured using commercial off the shelf (COTS) monodispersed gold (or silver)[14] nanoparticles 112 that is capped with amphiphilic molecules 130 on their surface by physical adsorption to impart them with hydrophobic properties. The length 132 of the capping molecules is selected as spacing materials from 0.5 nm to 10 nm for the precise control of the size of the nano-gap 118 when the molecules are in the close-packed format. The capping molecules are selected from donor ligands, linear polymer, surfactants and polyelectrolytes.

Figure 1C:
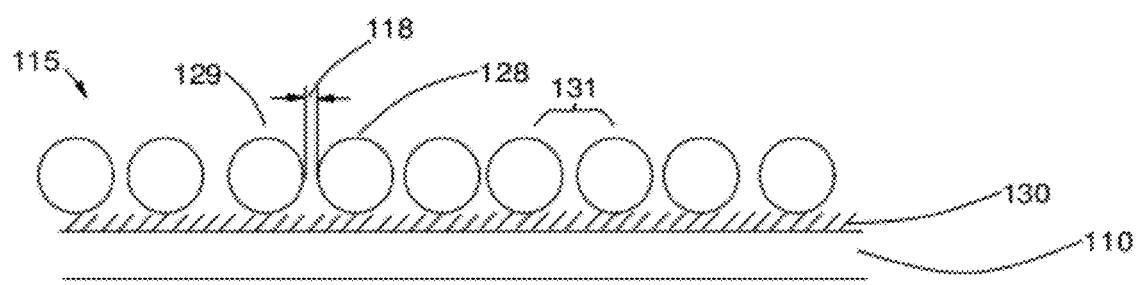
FIG. 1C illustrates a detail of FIG. 1B showing the nano-gap between nearest neighbor particles pairs.
Figure 1D:
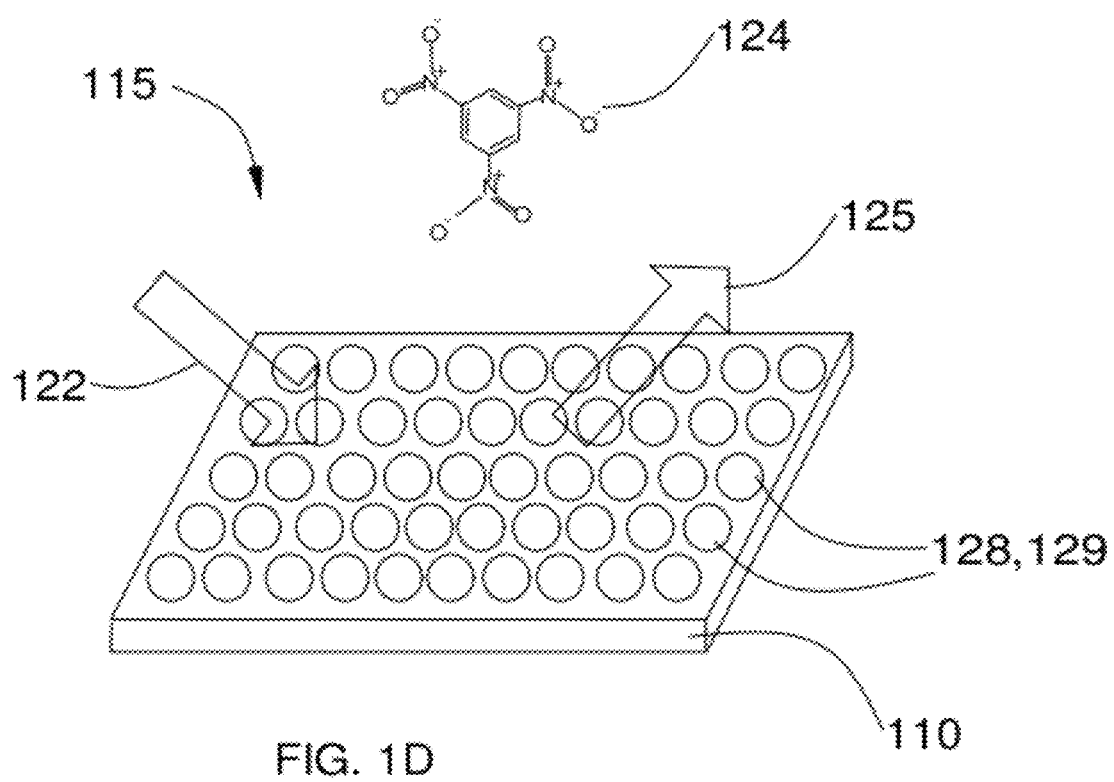
FIG. 1D illustrates incident and reflected light of a Plasmonic Nano-antenna Array (PNA).
Figure 1E:
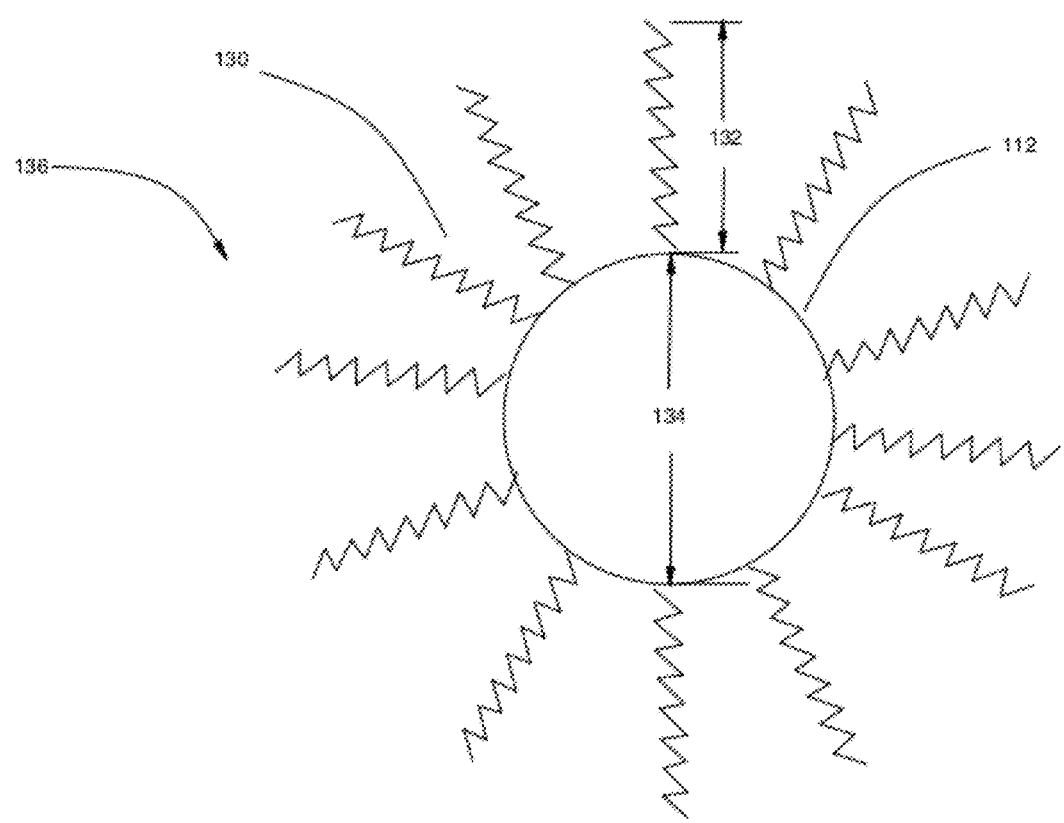
FIG. 1E illustrates a capped molecule.
Figure 1F:
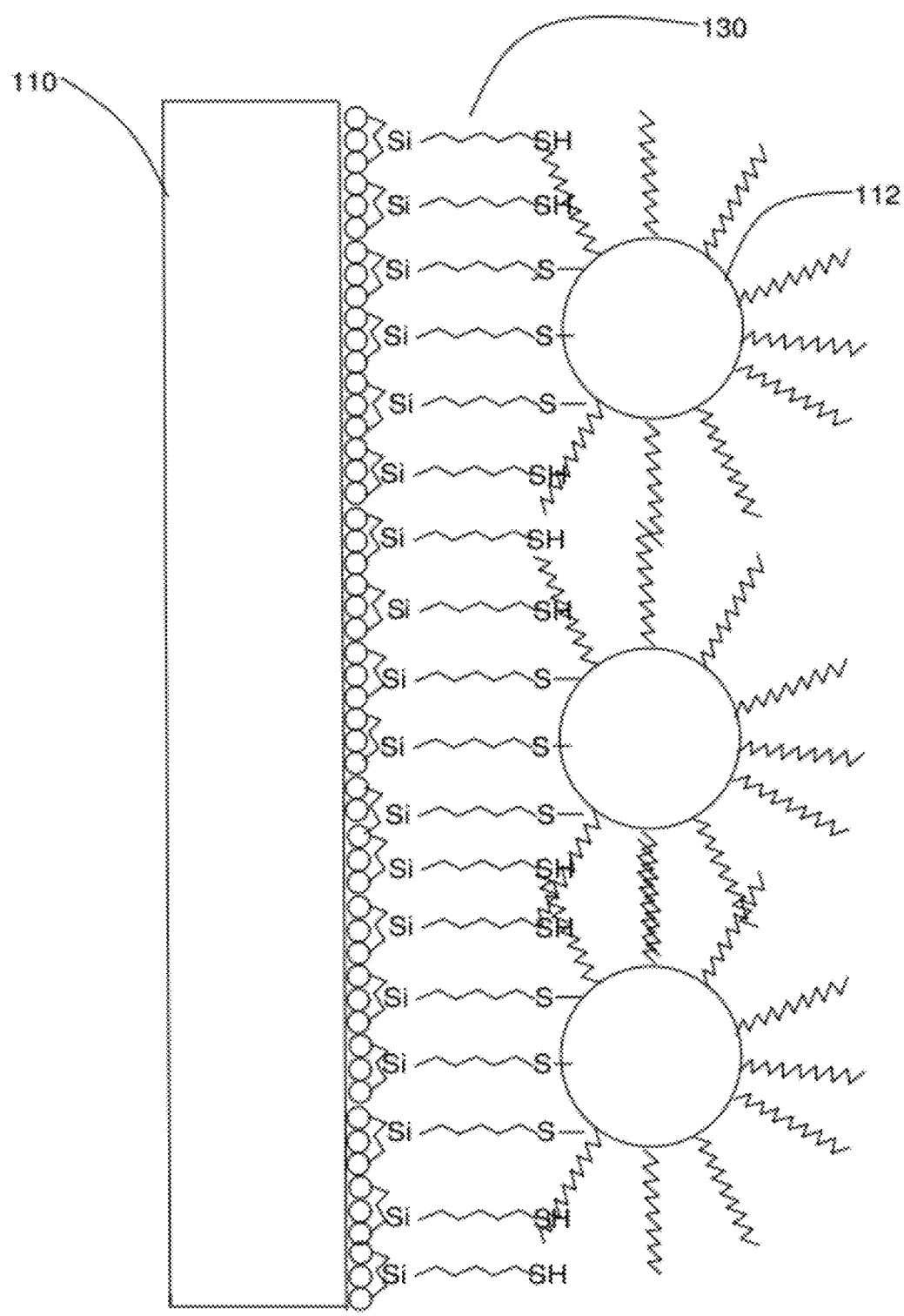
FIG. 1F illustrates a detailed structure of the PNA.

Referring to FIGS. 1A, 1E, 1F, a uniform, close-packed Langmuir monolayer of the capped nanoparticles 136 is obtained by spreading them on the water/air interface 138, followed by compression of the surface with computer controlled barriers 106 (FIG. 1A). A solid substrate 110 such as glass (or silicon wafer) is pretreated to form a pretreated glass surface 133 by self-assembling a thiol-terminated thin monolayer on its surface that is used to deposit the close-packed gold nanoparticle Langmuir monolayer on the glass substrate 110. The deposition process is precisely controlled using a computer and microbalance 146 to ensure a precise structuring of the nanoparticle array 115 with the desired nano-gaps 118. The controlled nanostructure is locked using a thiol-gold bond during the LB deposition process. The strong covalent thiol-gold bonds replace the weak physical adsorption bond of the local capping molecules as shown in FIG. 1F.

SURFACE ENHANCED RAMAN SPECTROSCOPY (SERS): Raman spectroscopy is a technique used to analyze the vibration, rotation, and other low-frequency modes of target molecules 124, thereby providing data for molecular/material identification. It relies on inelastic scattering, or Raman scattering 126, of monochromatic light, usually from a laser in the visible, near infrared, or near ultraviolet range, which has very weak signal strength.

Raman signals 126 for target molecules 124 (FIG. 1D) on a particular surface occur because of an enhancement in the electric field provided by the surface properties. When incident light 122 strikes the surface, localized surface plasmons are excited. The field enhancement is greatest when the plasmon frequency, $\omega_p$, is in resonance with the radiation. Furthermore, in order for scattering to occur, the plasmon oscillations must be perpendicular to the surface; if they are in-plane with the surface, no scattering will occur. It is because of this requirement that arrangements of nanoparticles 112 are typically employed in SERS experiments since these surfaces provide an area on which localized collective oscillations can take place.

The choice of nanoparticles 112 is dictated by the plasmon resonance frequency. Visible and near-infrared radiation (NIR) is used to excite Raman modes. Silver and gold are typical metals for SERS experiments because their plasmon resonance frequencies fall within these wavelength ranges, providing maximal enhancement for visible and NIR light.

In order to effectively couple the incident light to the surface plasmon modes leading to high local fields, metal nanostructures on the surface are specially engineered. Thus, metal nanostructured materials open new avenues for manipulating light and sensing molecules. Engineered plasmonic structures can act as "smart" optical nano-antennas focusing light on nanometer scale areas, with high spatial and spectral control of the energy concentration.

PLASMONIC NANO-ANTENNA ARRAY (PNA): A plasmonic nano-antenna 131 made of paired metal nanoparticles (dimer) can support a highly efficient, localized surface plasmon resonance and produce a significantly enhanced and highly confined electromagnetic field[5, 8, 15], which is also known as a "hot spot." These hot spots are critical for SERS. It is generally accepted that the duration of localized plasmonic excitations are determined by the type of metals and the shape of the nanoparticles 112 that are chosen[9-13]. Unlike single nanoparticle pair nano-antennas 131, nanoparticle array 115 can extend plasmonic lifetimes and can enhance near-fields effects due to the collective excitation of the plasmons. By harnessing these collective excitations, this design creates a new class of active plasmonic nanostructures which are highly effective for SERS-based sensing. The plasmonic nanoparticle array 115 can also be constructed with two or more layers to create a 3-dimensional configuration, providing even greater performance.

NANO-FABRICATION PROCESS TO CREATE THE PNA SURFACE: Studies have shown that large field enhancements are usually localized at the nano-gaps 118 of nano-antennas and that the enhancements improve dramatically when the gap size decreases below 5 nm[5, 8]. These studies are based on single molecule SERS experiments that typically use aggregates of colloidal nanoparticles where the "hot-spots" of enhanced local fields are obtained only by chance and are not controllable[3-7]. The particular challenge to achieving repeatable and controllable SERS active substrates originates from the difficulty of fabricating large-scale uniform arrays of nano-gaps 118 in a controllable and repeatable manner. The existing approaches employ MEMS fabrication processes that are extremely expensive and make these approaches non-cost-effective.

In contrast, the first embodiment of the present invention uses a proprietary nano-fabrication process that we call Langmuir-Blodgett Controlled Self-Assembly (LBCSA) technology to construct low-cost, scalable, controllable and reproducible plasmonic nano-antenna arrays. LBCSA is the critical process that leads to a feasible, cost-effective PNA fabrication.

Figure 2:
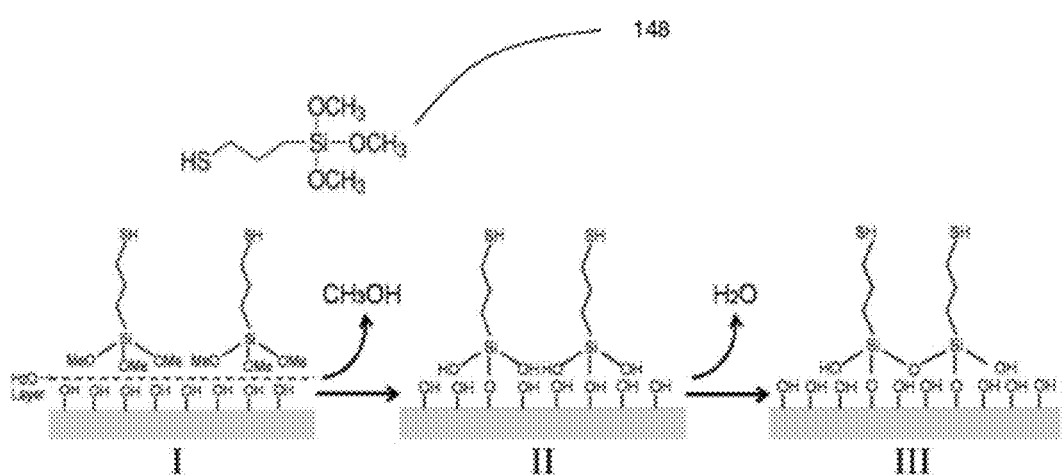
FIG. 2 gives a schematic of MPS monolayer formation on a hydroxylated silicon oxide surface.
Figure 3:
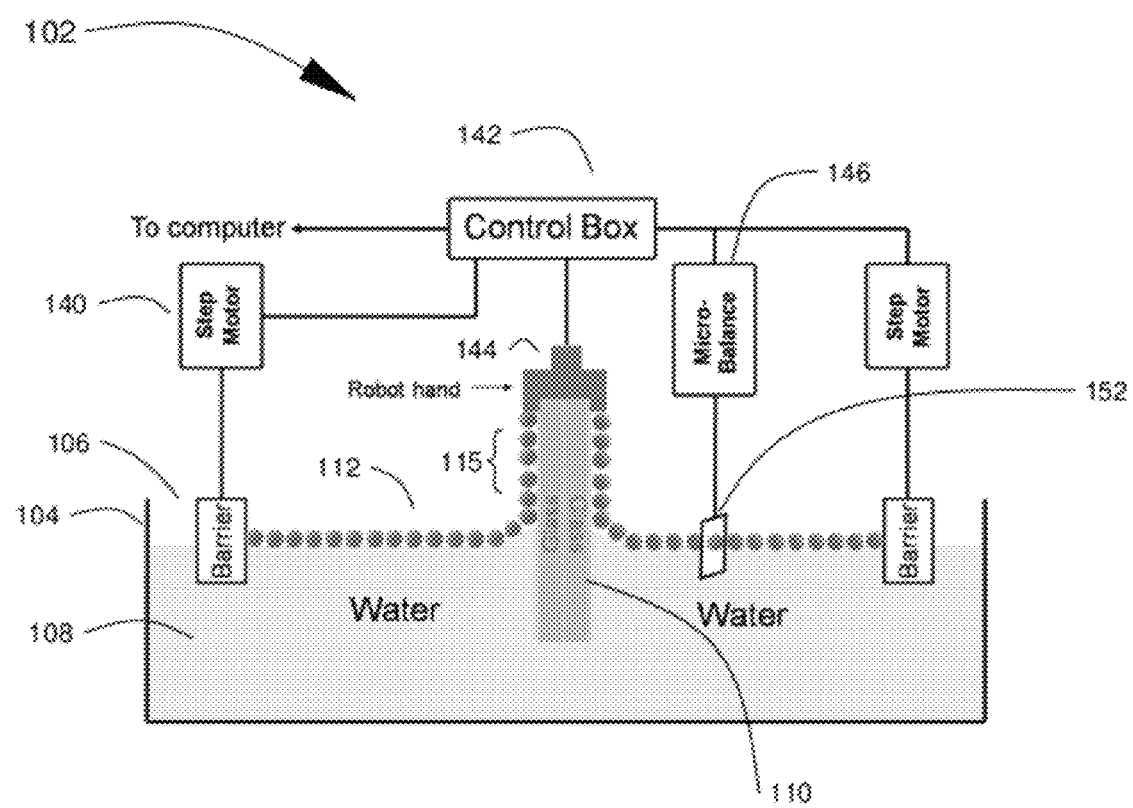
FIG. 3 is a schematic illustration showing a computer controllable Langmuir-Blodgett trough system having two troughs.

SURFACE MODIFICATION OF GLASS SUBSTRATE 110 WITH THIOL-TERMINATED GROUPS: FIG. 2 gives a schematic of MPS monolayer formation on a hydroxylated silicon oxide surface. FIG. 3 presents a schematic illustration showing a computer controllable water-filled Langmuir-Blodgett trough system 102 and deposition of successive gold nanoparticle layer (uniformly on top of thiol-terminated surface of two glass substrates simultaneously). As the first step in our fabrication process, a glass (or silicon wafer or quartz) substrate 110 is pretreated to form a pretreated surface 133 by self-assembling a thiol-terminated thin monolayer on its surface that is used to deposit a close-packed, strongly bonded, stable gold nanoparticle Langmuir monolayer on the pretreated surface 133. 3-Mercaptopropyltrimethoxysilane (MPS) 148 is used to form the thiol-terminated self-assembling monolayer 150 (SAM) on the glass substrate 110 because the silane end can bond to the silicon oxide glass surface while the thiol end can bond to gold nanoparticles. The MPS 148 self-assembly monolayer 150 (SAM) is directly formed on a hydroxylated silicon oxide substrates by exposure to 3-Mercaptopropyltrimethoxysilane vapor (MPS Vapor) followed by a dehydration process to cross-link the hydroxyl groups. MPS monolayers on $SiO_2$ are spontaneously formed via Si—O—Si bond formation such that the thiol groups face away from the oxide surface. FIG. 2 shows an idealized schematic of the steps believed to occur during MPS monolayer formation on a hydroxylated silicon oxide surface. This process can be applied to any molecules that have two functional ends: one end for the self-assembly formation of the monolayer on the surface (a solid substrate 110 as mentioned above or on a metal surface); and the other end for chemically bonding with the large molecules and particles (gold, silver or other organic or inorganic particles) that are assembled by LB technology.

LANGMUIR-BLODGETT TECHNOLOGY: In practice, the various approaches for plasmonic nano-antenna array fabrication are categorized into two directions: top-down and bottom-up. Top-down approaches encompass lithographic and MEMS etching techniques. The bottom-up approaches involve mostly self-assembly and self-organization. Examples of bottom-up approaches include chemical deposition, layer-by-layer (LBL) deposition, hydrogen bonding, and colloidal assemblies. There are also methods based on the combination of both bottom-up and top-down approaches, for example, casting of polymer solutions, phase separation and electro-spinning.

LB technology is a controllable molecular assembling technology that has wide applications in coating amphiphilic molecules 130, polymer ultrathin mono/multi-layers, and colloidal particles on diverse surfaces including glass and silicon wafer. A preferred embodiment of the present invention includes a new LBCSA process that is significantly different from LB technology and capable of cost-effectively assembling the required plasmonic nano-antenna array chemical bonded on the surface of glass.

Referring to FIG. 3, LB films are formed by the successive deposition of a series of mono-layers of one or more types of amphiphilic molecules 130 initially spread at the water/air interface 138. They usually consist of a regular planar array of molecular layers having a well-defined structure and predetermined thickness. LB film properties have made them of interest to physicists, electronic engineers, chemists and biologists[19]. The LB apparatus includes a water-filled Langmuir trough with a dipping device 144 that controls the dipping time and dipping rate that lower or raise the solid substrate 110 through a water/air interface 138, a barrier 106 that is automated and movable, which moves during the deposition process to maintain a controlled surface pressure, a control box 142, a step motor 140 and a surface pressure sensor 152 that controls the movable barriers. There has been progress reported on the robust monolayer fabrication of ligand-stabilized gold nanoclusters[20], semiconducting quantum dots[21] and polymeric films[22]. The water-filled Langmuir trough system may be replaced by a gas-liquid Langmuir trough system having a gas/liquid interface.

Unlike other technologies, LB technology can deposit a uniform/scalable nanoparticle layer on a solid substrate 110 in a controllable manner (FIG. 3). Due to its flexibility, low cost, and ability to accommodate multiple samples of various shapes simultaneously, the LB deposition process can also be scaled up for mass production. However, LB films are physically adsorbed on the substrate so that they are not stable and suitable for practical application.

The nano-antenna array structure is produced using commercial off the shelf (COTS) mono-dispersed gold (or silver) nanoparticles that are capped with amphiphilic molecules 130 on their surface by physical adsorption to impart them with hydrophobic properties. The length of the capping molecules is selected as spacing materials from 0.5 nm to 10 nm for the precise control of the nano-gap 118 size when the molecules are in the close-packed format. A uniform, close-packed, Langmuir monolayer of the capped nanoparticles 136 is obtained by spreading them on the water/air interface 138, followed by compression of the surface with computer controlled barriers 106. An appropriate surface pressure is selected for the LB deposition. A similar approach has been reported by Tredgold, et. al. by assembling a mono-dispersed silica nanoparticle (300 nm) monolayer successfully onto a solid substrate[23]. The preferred embodiment LBCSA process uses the LB technology to control the nanoparticle array 115 and to deposit the array onto a thiol-terminated (or functionalized) surface of a substrate rather than a bare surface, followed by a self-assembly surface reaction (such as a thiol reaction) to form a chemical bond between the nanoparticle array 115 and the solid surface.

LANGMUIR-BLODGETT CONTROLLED SELF-ASSEMBLY TECHNOLOGY (LBCSA) AND 2-DIMENSIONAL PLASMONIC NANO-ANTENNA ARRAY: Unlike the MPS molecules and other SAM molecules, gold nanoparticles are not able to spontaneously form a uniform layer on a substrate surface. The driving force for the spontaneous formation of the 2D SAM includes chemical bond formation of molecules with the surface and intermolecular interactions, which are much less controllable in forming artificial order structures. The order in these two-dimensional systems is produced by a spontaneous chemical synthesis at the interface as the system approaches equilibrium. The system equilibrium state depends on many different factors such as molecular conformation, temperature, and bonding affinity to the surfaces. For instance, sulfur and selenium compounds have a strong affinity for transition metal surfaces, Organosulfur compounds coordinate very strongly also to silver, copper, platinum, mercury, iron, nanosize γ-Fe2O3 particles, colloidal gold particles, GaAs, and InP surfaces.

The required spontaneous yet ordered thin film structure of gold nanoparticles is very difficult to produce because the film's affinity to the surface and its internal interaction among molecules is often beyond control. However, to overcome this difficulty, we first use external force to compress the molecules and guide them into a desired structure on the water/air interface 138, and then transfers the molecules to an active pre-conditioned solid surface to which the molecules have strong affinity. As indicated, the approach uses a combination of LB and SA technologies. The periodic uniform structure formed on the water/air interface 138 using external force is lost if the external force is surface is repeatedly deposited on the thiol-terminated glass surface 133. The deposition process is precisely controlled using a computer and microbalance 146 to ensure a precise structuring of the nanoparticle array 115 with the desired nano-gaps 118. The controlled nanostructure is locked using a thiol-gold bond during the LB deposition process. The strong covalent thiol-gold bonds replace the weak physical adsorption bond of the local capping molecules as shown in FIG. 1F.

The LBCSA process of the preferred embodiment of the present invention is different from the pure LB or SA methods. The pure LB technology can only deposit a monolayer that is physically adsorbed on the solid substrate, so it would be unstable for practical application in the preferred embodiment of the present invention. Unlike the pure LB or SA processes, the LBCSA process can be applied to any large molecules or particles even if they are unable to undergo normal self-assembly in a uniform 2D structure on a solid substrate.

PROCESS FOR FABRICATION OF NANOPARTICLE MATRIX PATTERNS OF PNA ARRAY: The PNA technology is intended to fabricate a range of different nanoparticle matrix patterns for the plasmonic nano-antenna arrays designed to operate at alternative Ramon scattering laser light frequencies, thereby allowing access to multiple types of excitation laser sources. FIG. 4 shows four processes based on the PNA technology, each leading to a different matrix pattern.

Figure 5:
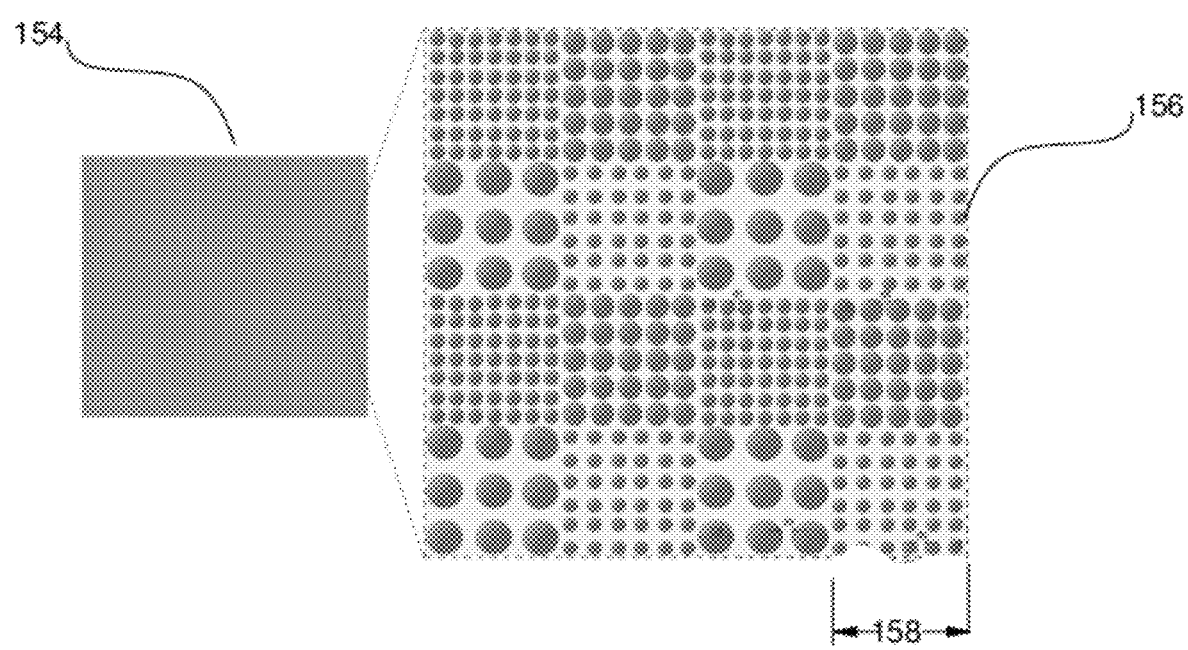
FIG. 5 illustrates a detailed view of FIG. 4 illustrating the fabricated matrix pattern.

FIG. 4 illustrates a process based on the PNA technology to fabricate a matrix pattern for multiple excitation purpose. Three columns represent mask alignment process (step 1, 4, 7, and 10), self-assembly process for modify substrate surface (step 2, 5, 8 and 11) and our LBCSA process to fabricate plasmonic nano-antenna array based pattern on glass (step 3, 6, 9, and 12). The four rows show steps I, II, III and IV for the configuration four different matrix pattern respectively, each matrix pattern has different structure in terms of gold particle diameter 138 and dimer gap 118. Each matrix pattern is obtained in a repeatable manner on units of micron size 158 (<5 μm) and is formed with a different nanoparticle array 115 in terms of nano-gap 118 and particle size 134. Referring to FIG. 5, the fabricated matrix pattern 154 is illustrated with a matrix pattern detailed view 156.

The fabrication process based on PNA technology is feasible and well-suited to this application. With help of a pre-designed micro-precision mask that is obtained by conventional laser machining, MEMS or Polydimethylsiloxane (PDMS)-based lithography technology, a sophisticate matrix pattern is readily fabricated to facilitate the multiple excitation applications. In Step I, the patterned thiol-terminated SAM on glass is assembled by covering the glass with the mask and following the process shown above. Then, the nanoparticle array is assembled onto the SAM pattern using the LBCSA process. Strong covalent bonds can only be formed in the area of the SAM pattern, which locks-in the desired structure formed by the LB technology. Other areas without the SAM pattern only have some physically adsorbed particles that is removed via a sonication process. By flipping the mask, realigning it on the glass and following Steps I, II, III and IV, each matrix pattern is configured. Finally, a sophisticated structure like the one shown in FIG. 5 (b) is obtained. It's important to note that this process is organized into an assembly line for mass production and that the PNA technology has potential to fabricate nanostructures for many other useful applications, such as supper lenses, negative refractive index materials, meta-materials, plasmonic devices, enhanced optical transmittance, plasmonic nano-lithography, disorder-induced localization of plasmons, and surface-enhanced nonlinear optical phenomena.

LBCSA PROCESS INNOVATIONS: The LBCSA process has the following differences and advantages over other approaches:

Controllability: The crystal-like gold nanoparticle array and the nano gap between the nearest neighbor particles is precisely controlled at the nanometer level by selection of appropriate capping molecule length and by computer controllable LB techniques.

Repeatability: The gold nanoparticle Langmuir monolayer is precisely controlled using the LB trough. The repeatable process and resulting structure of such monolayers has been extensively studied and reported in the scientific literature. The Langmuir structure is transferred and locked on the pretreated glass surface 133 without losing the designed nanostructure.

Scalability: The PNA array can reach a size of 10 cm$^2$ or higher. The LB facility is easily scaled up to any size to facilitate a large amount of deposition for mass production.

Stability: The plasmonic nano-antenna structure formed originally on the water surface is locked onto the thiol-terminated glass surface 133 with a strong thiol-gold covalent bond, which ensures that the nanostructure is stable on the surface.

Low cost: Unlike the current MEMS fabrication process, PNA technology does not need any expensive etching and lithography processes. The LBCSA technology is very cost effective.

Diversity: The PNA technology is used not only to fabricate nano-antenna structures on flat substrates, but also on non-flat substrates including optical fibers to facilitate the development of future portable SERS instruments.

Nonhazardous: The process for fabricating the plasmonic nano-antenna array doesn't require any hazardous solvents or materials. The gold nanoparticles is transferred onto the substrate without waste using LB deposition techniques.

These advantages are made possible by the following unique our innovations:

Application of LBCSA deposition technology to sequentially deposit monolayers of gold nanoparticles onto the glass surface; and Incorporation of a thiol-gold reaction during the LB deposition process.

Figure 6A:
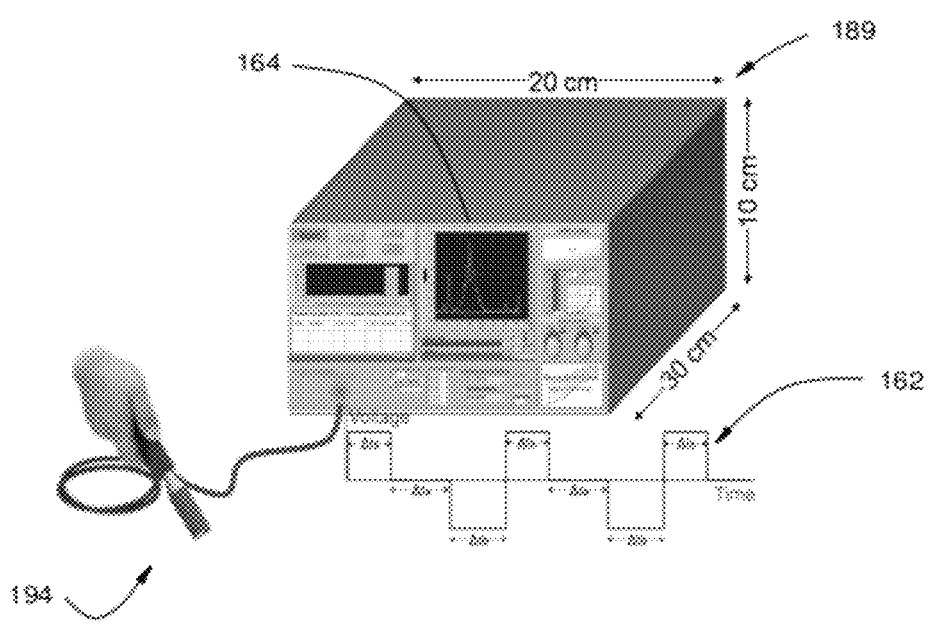
FIG. 6A is a predesigned nano-antenna based Raman-Scattering Gas Sensor using our Raman sensor system and a nano-antenna array substrate.
Figure 6C:
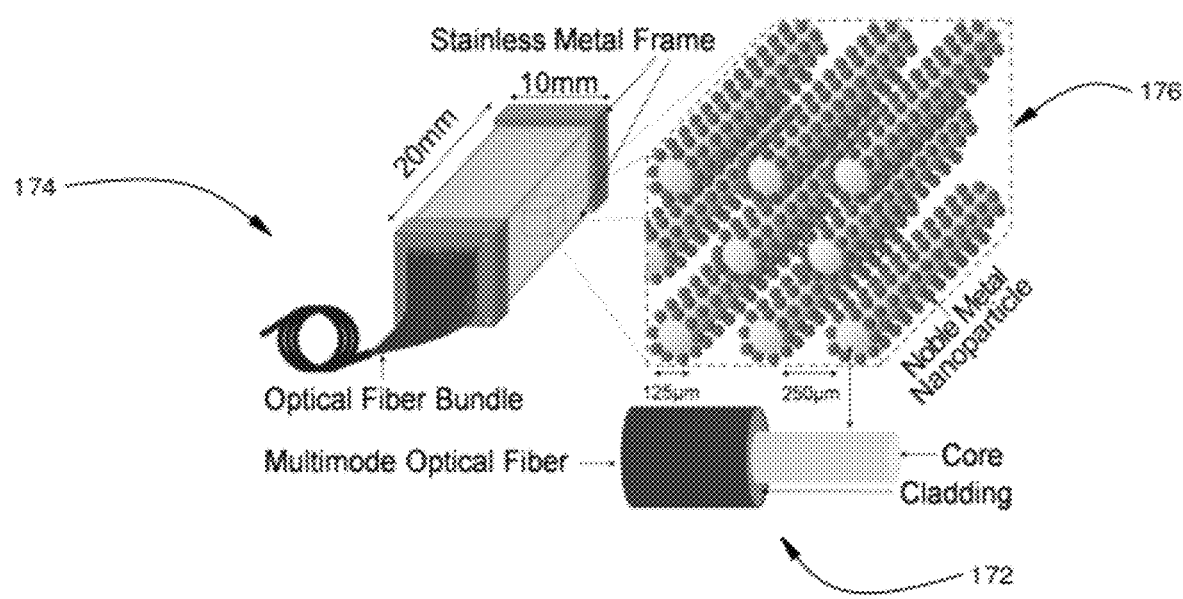
FIG. 6C illustrates the predesigned fiber optical gas sensor head including a unique air suction design and nano-antenna SERS active substrate with optical precision adjustable holder.
Figure 6D:
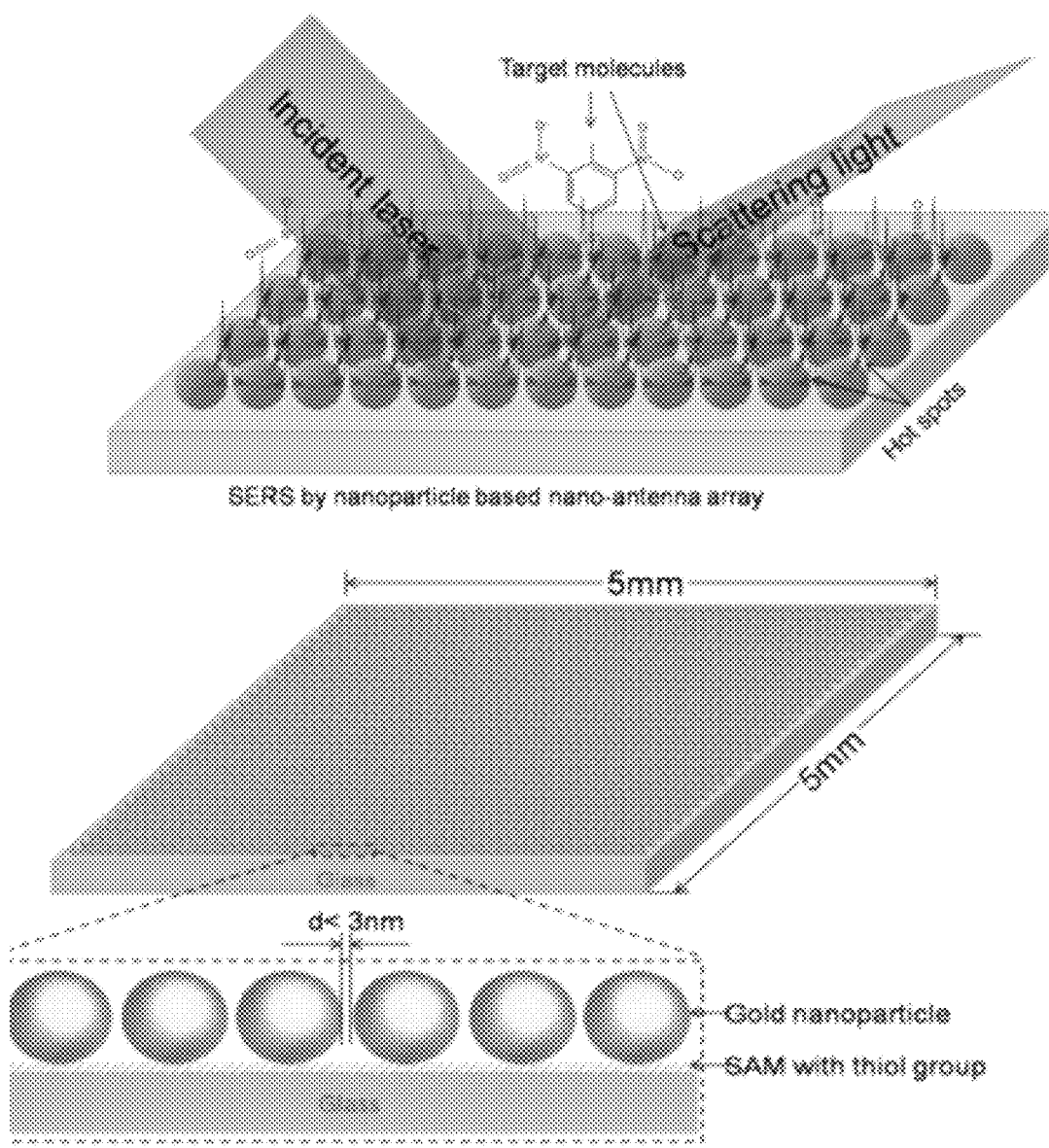
FIG. 6D illustrates the principle scenario and a detailed nanostructure of the nano-antenna array substrate.

SYSTEM FOR USING PNA-BASED SERS TECHNOLOGY: FIGS. 6A through 6D schematically illustrates the design for a plasmonic nano-antenna array and Raman scattering gas sensor system and shows its operational mode: FIG. 6A illustrates the scenario and profile of the predesigned nano-antenna based Raman-Scattering Gas Sensor using our Raman sensor system and a nano-antenna array substrate 111. The screen 164 located on the Ramen apparatus 189 displays the spectrum of data profiles of the Raman spectrum data obtained from target molecules; the insert 162 is a schematic drawing of the system operational mode. FIG. 6B illustrates the main components of the Ramen instrument including air suction system 168, diode laser system 166, and spectrometer system 170. The system operation is controlled by in house developed system software through a portable USB data acquisition card and a data base system for saving, comparing and analyzing the conformation profile of detected molecules=FIG. 6C illustrates sensor head 174—the predesigned fiber optical gas sensor head 172 including a unique air suction design, nano-antenna SERS active substrate with optical precision adjustable holder A noble Metal Nanoparticle detail 176 of the nano-antenna SERS active substrate with optical precision adjustable holder. FIG. 6D illustrates the principle scenario and detailed nanostructure of the nano-antenna array substrate 111. Detection is determined by a best match of Raman spectrum data obtained from target molecules to previously stored Raman spectrum data of the molecules of interest.

FIG. 6C is the critical component—the sensor head 174. The detailed design of the sensor head 174 includes the optical design, nano-antenna array substrate 111 and its holder, and an air flow channel. The incident light 122 from the diode laser 160 is guided to the nano-antenna array by an optical fiber and a lens. The scattered light is collimated and subsequently focused towards the spectrometer employing achromatic lenses. For spectral dispersion and detection of the signal, a compact spectrometer system with an embedded, air cooled CCD chip is used. A colored glass filter is installed to suppress elastically scattered laser light. The detector chip is back-thinned and achieves high quantum efficiency and hence a high signal-to-noise ratio. The spectrometer can obtain 0.74 nm pixel—1 spectral resolution utilizing a reflective grating.

FIG. 6D, a composite figure of FIGS. 1B, 1C and 1D, shows the principle scenario and detailed nanostructure of the nano-antenna array substrate made using a proprietary nano-fabrication process called Langmuir-Blodgett Controlled Self-Assembly (LBCSA) technology. This technology provides the controllable and repeatable fabrication process that is needed for production. Such large-scale, highly SERS-active substrates can only be obtained by assembling a crystal-like gold or silver nanoparticle array 115 on a glass or silicon wafer substrate using the LBCSA fabrication technology. Using this technology, the gap between the nearest neighbor particles can be precisely controlled at the nanometer level (<3 nm) (FIG. 6 D), thereby rendering these particle pairs (dimers) as plasmonic nano-antennas 131 with large local field enhancements (estimate $E/E_0$>100). The entire surface of the large scale substrate (up to 10 cm$^2$) are covered with these nano-antennas in the form of a close, compact array, which creates a correspondingly close-packed "hot spot" array covering the solid substrate surface 113. Any molecule loaded on the SERS active surface arrive at one of the "hot spots" for high SERS enhancement because the close-packed "hot spot" array covers the entire SERS surface.

Figure 7A:
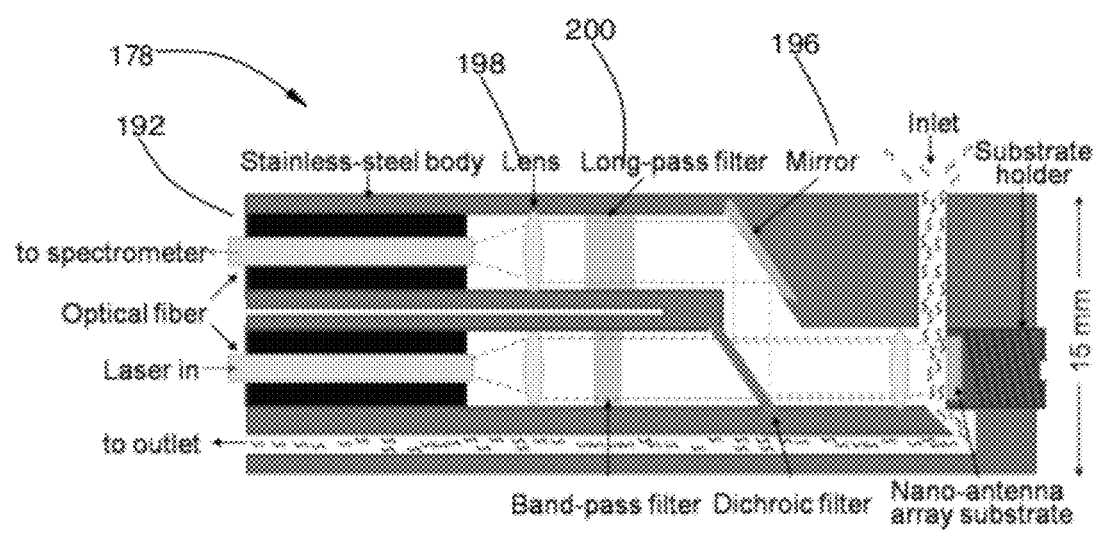
FIG. 7A illustrates the pre-design nano-antenna & optical fiber based sensor head.
Figure 7B:
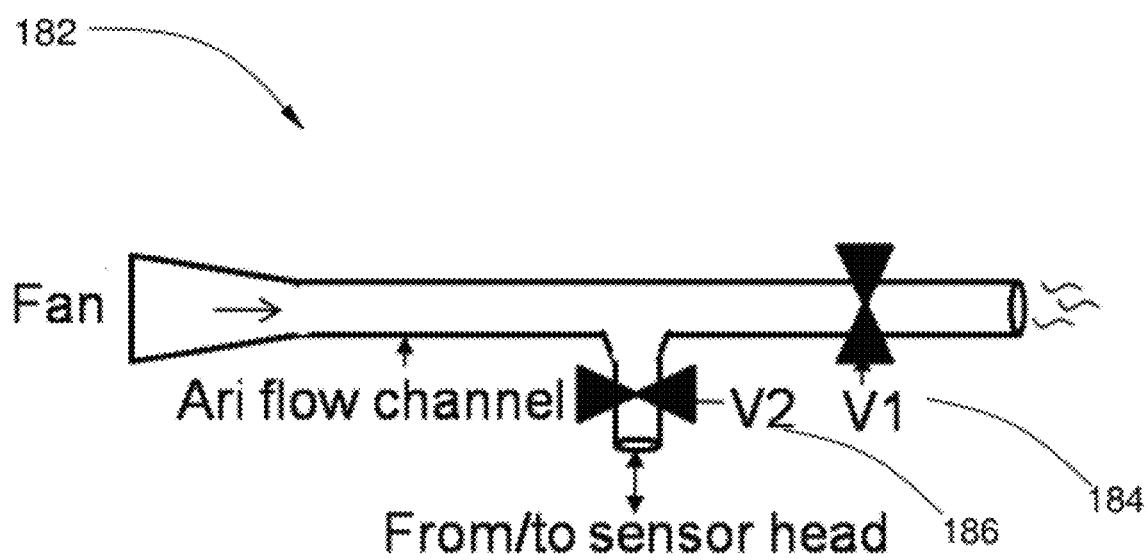
FIG. 7B illustrates the detail design of the sample collection device.
Figure 7C:
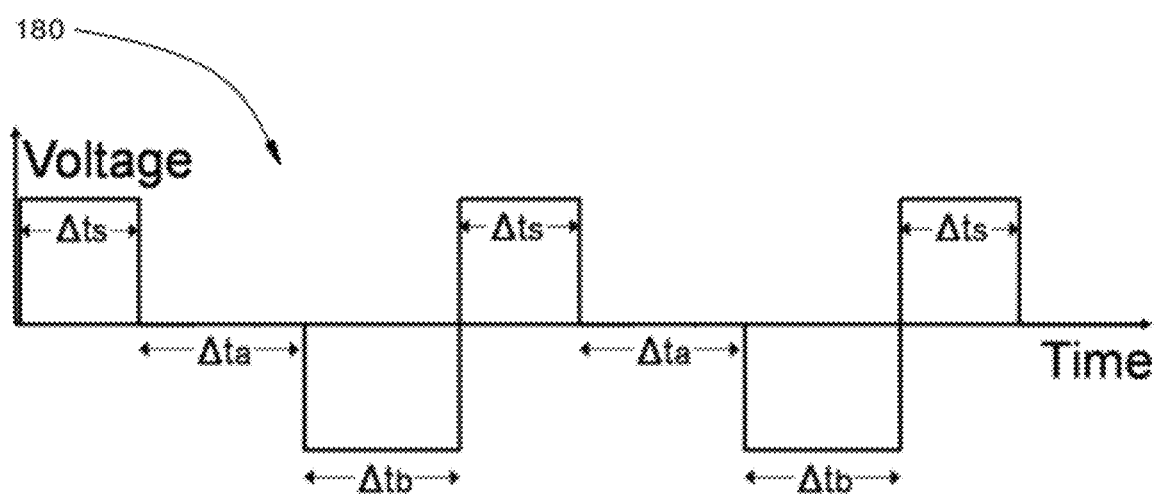
FIG. 7C illustrates the working mode of the sample collection device.

FIG. 7A presents the pre-design nano-antenna & optical fiber based sensor head 178. FIG. 7B presents the detail design of the sample collection device, FIG. 7C presents the working mode 180 of the sample collection device.

Based on the nano-antenna array SERS substrate concept, the preferred embodiment of the present invention includes an ultra sensitive, high resolution and compact Raman-Scattering gas sensor system. The main mechanical parts of the sensor are the laser system, the spectrometer and the sensor head 174. In general, the excitation wavelength for linear Raman spectroscopy can be chosen arbitrarily. However, the Raman scattering 126 cross section is a strong function of the laser wavelength. It significantly increases with the laser frequency. Therefore, short wavelengths are usually favored for Raman spectroscopy in order to gain high signal levels. A number of compact standard lasers can be employed in the system design. The output of the laser is controlled using a simple potentiometer. The entire laser system, including the laser head as well as two power supply units, have a low total weight. The scattered light is collimated and subsequently focused towards the spectrometer employing achromatic lenses. For spectral dispersion and detection of the signal, a compact spectrometer system with an embedded, air cooled CCD chip is used. A colored glass filter is installed to suppress elastically scattered laser light. The detector chip is back thinned and achieves high quantum efficiency and hence a high signal-to-noise ratio. The spectrometer can obtain 0.74 nm pixel—1 spectral resolution utilizing a reflective grating.

The sensor head 174 is illustrated in FIG. 7A. It is made of stainless steel and employs an interference-type filter to remove the Raman background before the laser light strikes the sample adsorbed on the nano-antenna array. It also removes most of the Rayleigh line from the light scattered off the sample before entering the collection fiber. The nano-antenna array substrate 111 is installed in an optical precision-adjustable sample holder for precisely positioning the nano-antenna array on the focal point of the incident laser. The gas sample is drawn into the air flow channel 182 and adsorbed on the nano-antenna array for analysis. FIGS. 7B and 7C show the sample suction device with two electronic valves (first electronic valves V1 184 and second electronic valves V2 186) and the sampling mode including sample suck-in period $\Delta t$ (both first electronic valves V1 184 and second electronic valves V2 186 open), the sample adsorption period $\Delta t_a$ (first electronic valves V1 184 open and second electronic valves V2 186 close) of sample adsorption to the nano-antenna array for SERS, and the sample blow-out period $\Delta t_b$ (V1 close and V2 open) of blow-out the sample from the nano-antenna array. This sampling operation mode simulates the bloodhound sniffing action. The data are collected periodically many times and averaged for obtaining a high confidence level for accurate detection.

Figure 8B:
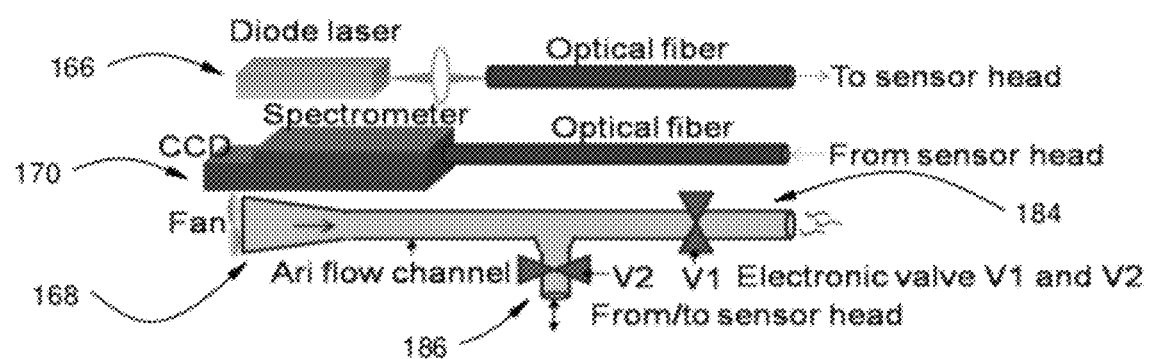
FIGS. 8A through 8E present the 3D nano-antenna array Raman scattering sensing system.

3-DIMENSIONAL PNA SENSING SYSTEM: As an alternate embodiment, the nano-antenna array can be built in a 3-Dimensional (3D) format that can further enhance the Raman scattering signal strength and increase the probability up to the 100% level for capturing the target molecules 124 in the antenna hot sport array. As shown in FIGS. 8A through 8E, the target molecules 124 are guided by an air samples passing through a special head gas flow channel using a air vacuum pump 125 through the 3D nano-antenna array (FIG. 8C). The excited hot spots fill the entire channel so that the passing target molecules 124 cannot avoid interacting with them. The substrate for the deposition of the 2D nano-antenna array is quartz that has very good optical band pass performance in the visible region and so doesn't absorb visible light. It only serves as a holder to form the 3D nano-antenna array with parallel gas flow channels. The 3D nano-antenna array is assembled by parallel arrangement of the 2D nano-antenna array and fixed with a stainless steel frame 192 (FIG. 8D). FIG. 8E shows a side view of the 3D nano-antenna array and the detailed structure of the 3D nano-antenna array with gas flow channel respectively.

Figure 8A:
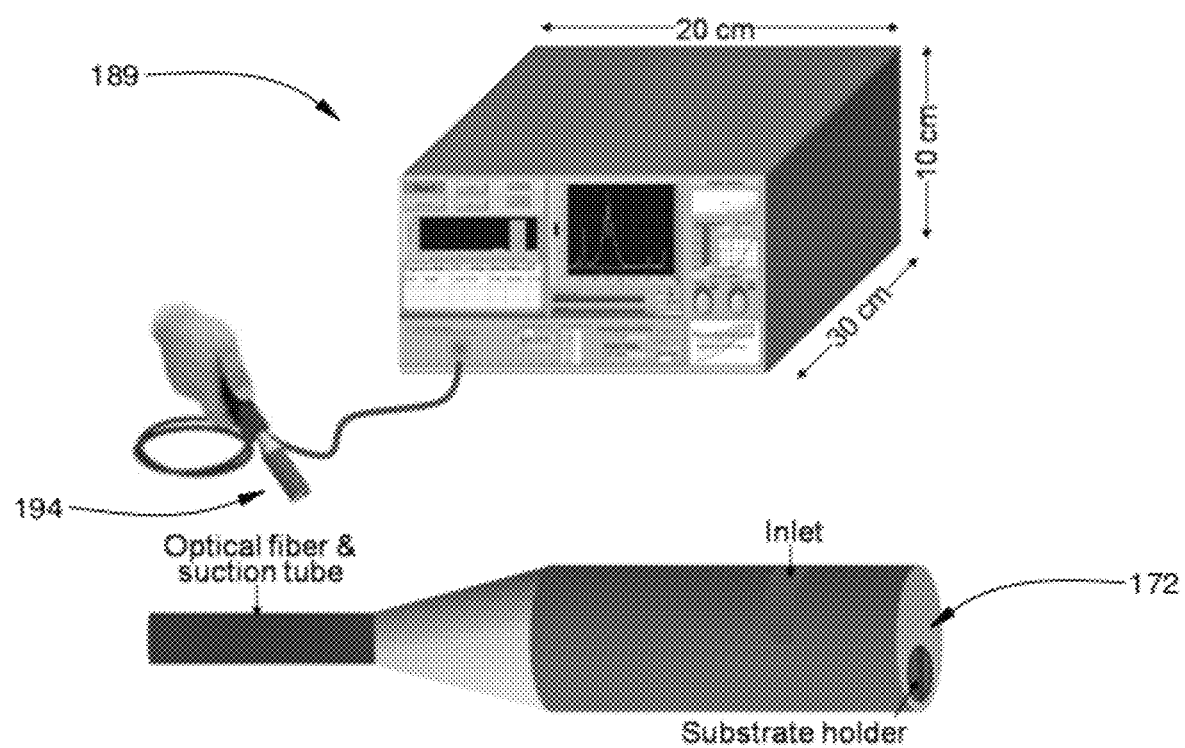
Figure 8B:
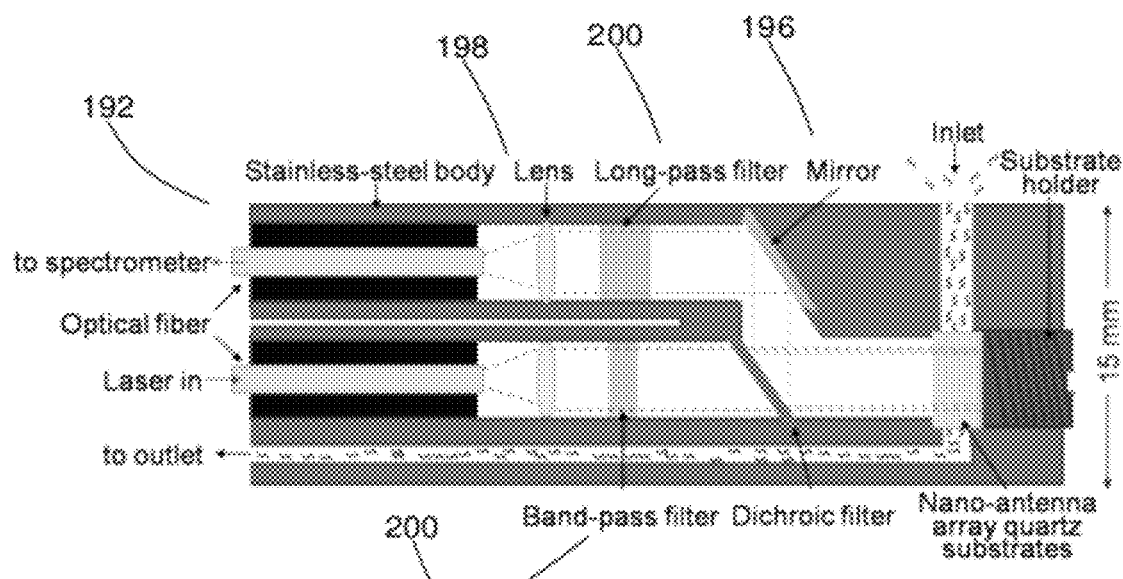
Figure 8C:
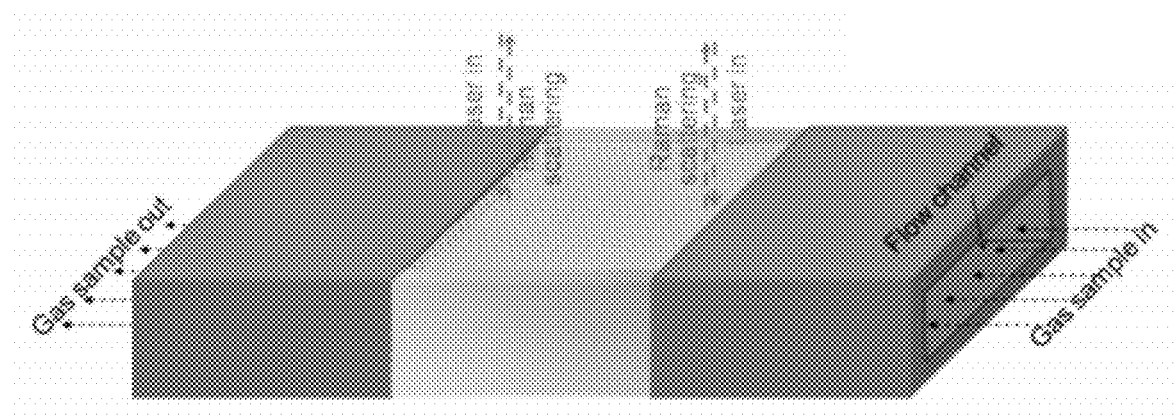
Figure 8D:
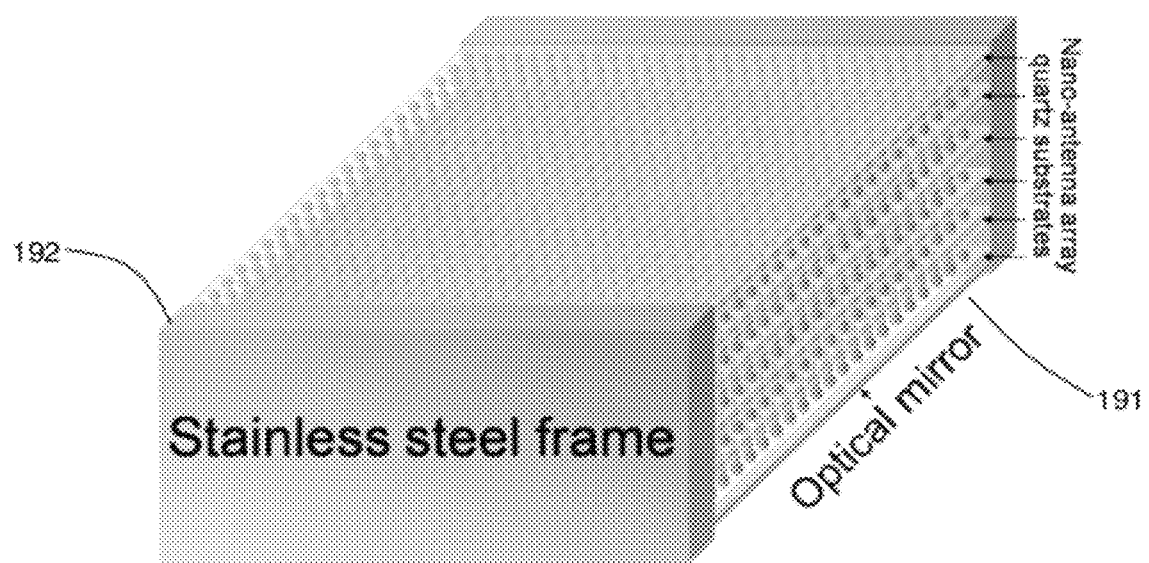
Figure 8E:
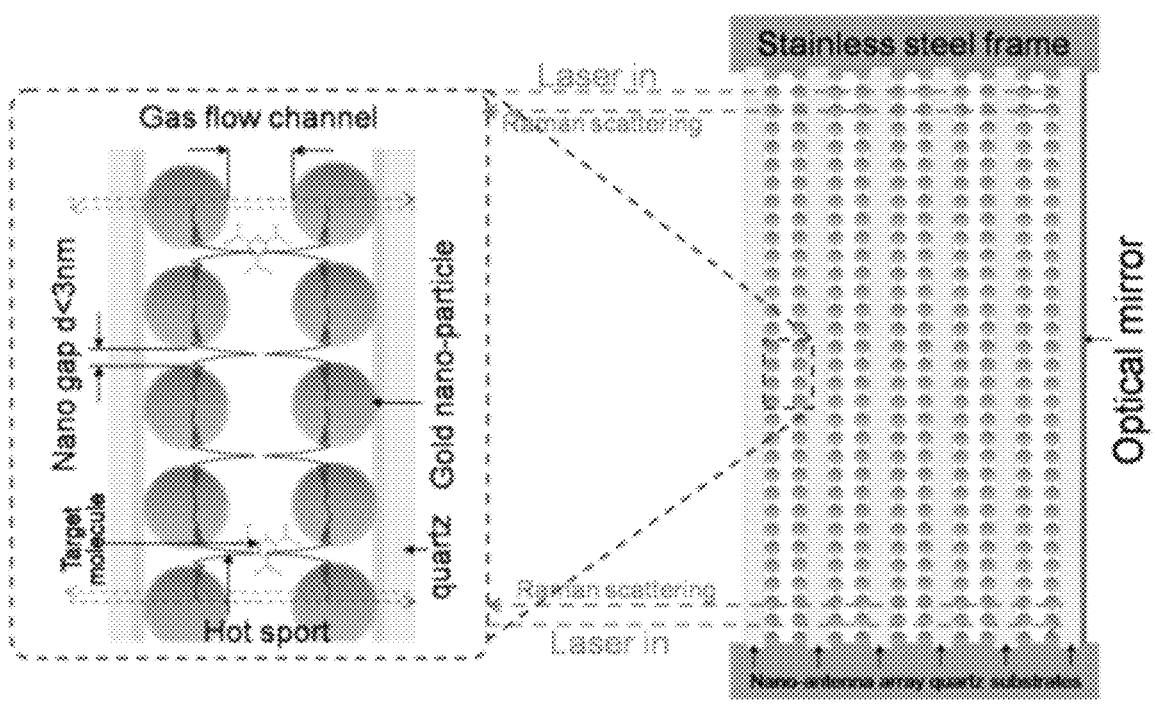

FIG. 8A illustrates the components of the 3D nano-antenna array Raman scattering sensing system: The design of the Raman system FIGS. 8A and 8B is the same as that described in FIG. 6 except for the 3D nano-antenna array structure instead of 2D nano-antenna array structure. The 3D nano-antenna array based SERS substrate is assembled with many 2D nano-antenna arrays deposited onto the quartz substrates using the LBCSA process FIGS. 8B, 8C 8D and 8E. FIG. 8C shows the design of the 3D nano-antenna array substrate with gas flow channels 190 for guiding the sample through the multi-channel array. The nano-gap 118 between two adjacent 2D nano-antenna array 188 gas flow channels 190 can be varied from a few tens of microns to a few tens of millimeters according to the application requirements. FIG. 8D illustrates the optical minor 191 embedded in a stainless steel frame 192. FIG. 8E shows a side view of the 3D nano-antenna array 188, and also shows the detailed structure of the 3D nano-antenna array with its gas flow channels 190.

The embodiments of the present LBCSA process invention presented herein employ a substrate surface that is modified using a thiol-terminated monolayer as described above in SURFACE MODIFICATION OF GLASS SUBSTRATE WITH THIOL-TERMINATED GROUPS. Other embodiments are also consistent with the inventive concept presented herein. For example, the process can be applied to many types of physical surfaces, including glass, quartz and various metals, using any molecules that have two functional ends: one end for the self-assembly formation of the monolayer on the surface, and the other end for chemically bonding with the larger molecules and particles, such as gold, silver or other organic or inorganic particles, that are to be assembled and deposited via LB technology. The LBCSA process can also use substrates modified with different functionally-terminated groups such as the silane group for silica nanoparticle deposition. Using the LBCSA process, a stable and controllable multilayer of nanoparticles can be created by repeating the process of adding a new layer of the functionally-terminated groups to the surface, followed by depositing a compatible nanoparticle layer above it. Since the process is non-lithographic, it can be used to fabricate many types of three-dimensional nanoparticle arrays including photonic crystals, phononic crystals and plasmonic devices. The process can also apply to metal nanoparticles, polymer nanoparticles, semiconductor nanoparticles, and metal oxide nanoparticles in a controllable manner.

Figure 9A:
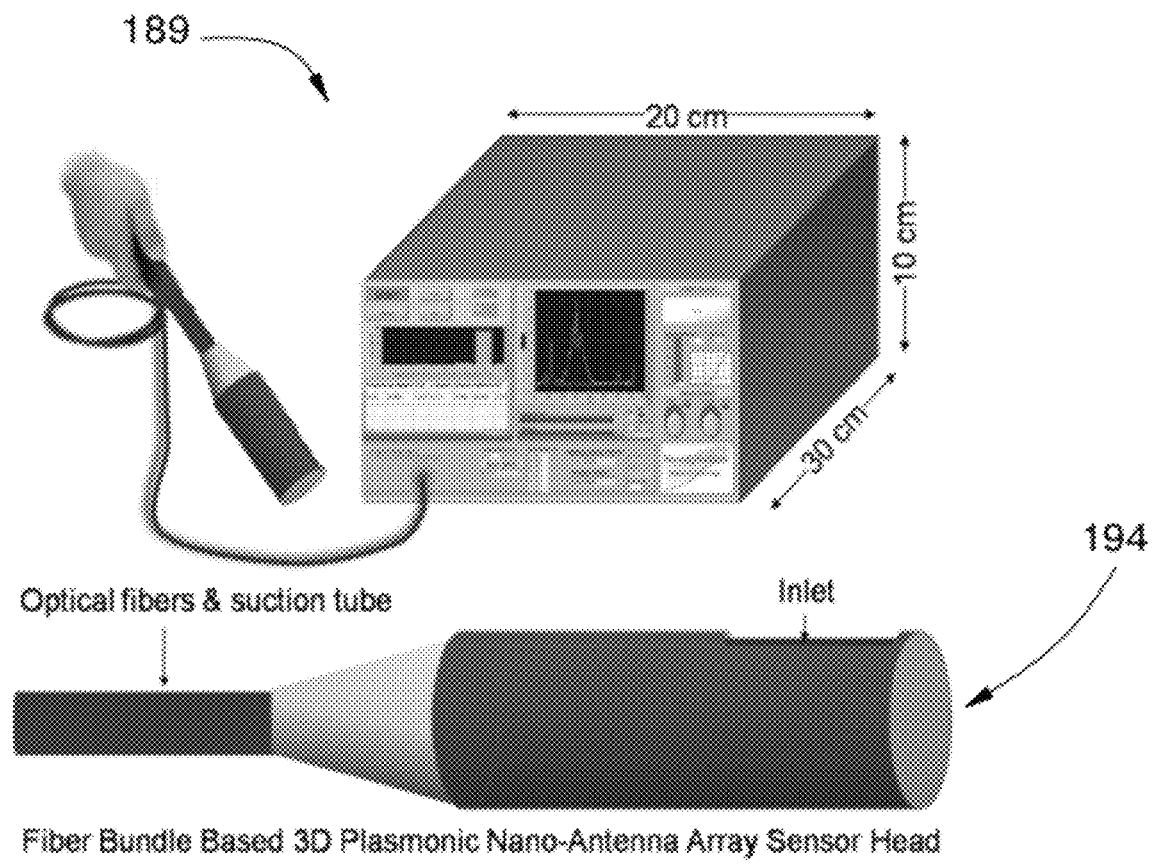
FIGS. 9A through 9D present another embodiment of a 3D nano-antenna array Raman scattering sensing system.

A second embodiment of the gas sample sensor and analysis system, including Raman spectrometer, microcomputer, suction head and wand, and database is shown in FIGS. 9A through 9D. Referring to FIG. 9A, this embodiment includes a plasmonic nano antenna fiber optic bundle 194 in place of the nano antenna array of the first embodiment in order to further enhance the sensitivity of the Ramon spectrometer signal in the system. The database stores a set of molecular spectrum profiles.

A plasmonic nano-antenna array can be deposited onto a polished optical fiber core surface using the LBCSA process as described above. The polished optical fiber core surface is polished by an annular polishing technique. Using this technology, the nano-gap 118 between the nearest neighbor particles can be precisely controlled at the nanometer level (<3 nm) using a precision sensing unit, thereby rendering the particle pairs (dimers) as plasmonic nano-antennas on the optical fiber core surface with large local field enhancements (estimate $E/E_0>100$). The entire surface of a polished fiber optic bundle can be covered with these nano-antennas in the form of a close, compact array. The plasmonic nano-antennas each create a highly efficient, localized surface plasmon resonance and produce a significantly enhanced and confined electromagnetic field which is known as a "hot spot."

Figure 9B:
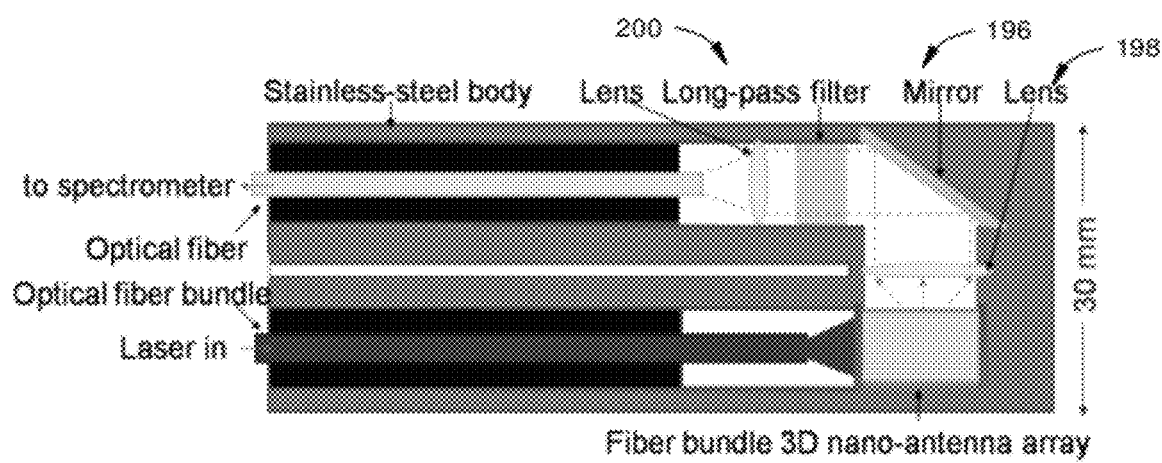
Figure 9C:
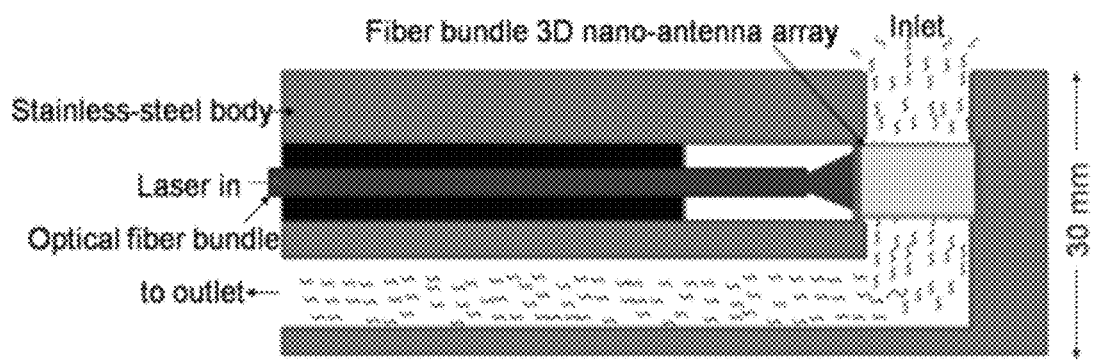
Figure 9D:
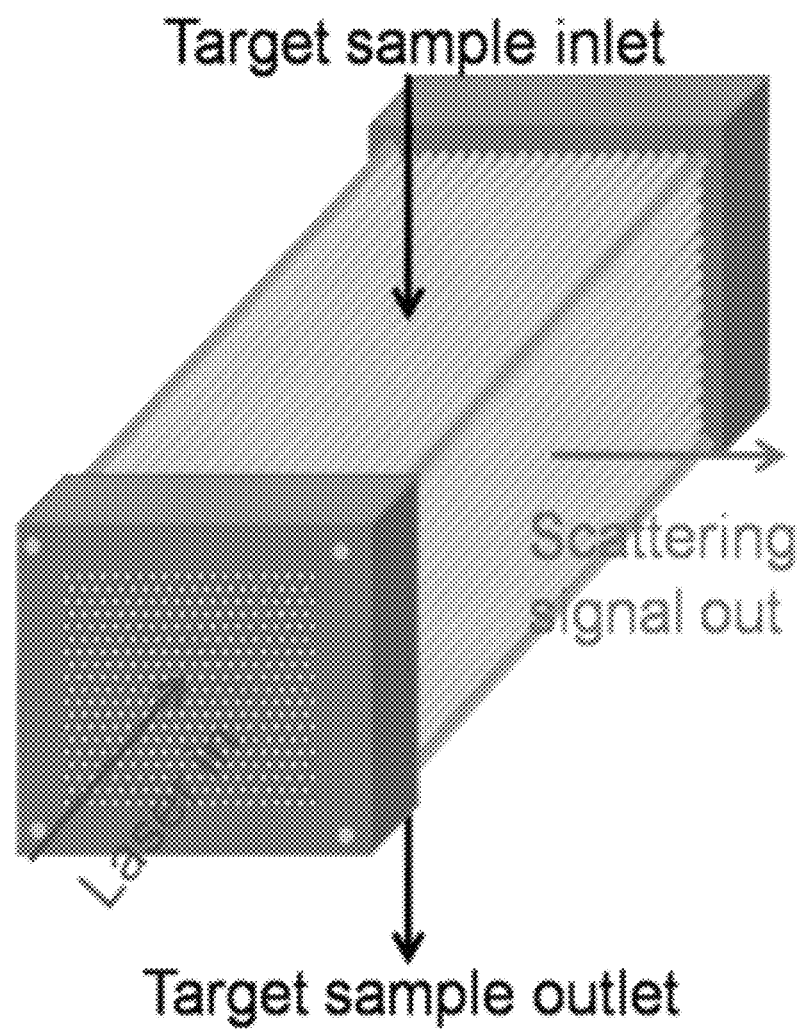

Multiple optical fibers with the deposited nano antennas can be combined to form an optical fiber bundle 202 as shown in FIG. 9D. Inside the gas sensor head of the second embodiment, the target gas sample molecules are drawn in and guided via a gas flow channel through the nano-antenna fiber optic bundle array 204 (FIG. 9C). Laser light is guided through the nano-antenna fiber optic bundle array on its way to the Raman spectrometer by employing a series of optical mirrors 196, optical lenses 198 and filters 200 (FIG. 9B).

The plasmonic nano antenna fiber optic bundle array increases the Raman scattering signal strength and also increase the probability of capturing the target molecules 124 in the antenna hot spots to nearly 100%. The excited hot spots fill the entire gas flow channel so that the passing target molecules cannot avoid interacting with them. The plasmonic nano-antenna array is assembled by parallel arrangement of the antennas on the optical fiber core surfaces and by fixing them in place with a stainless steel frame 192.

REFERENCES

REF. 1: J. I. Steinfeld and J. Wormhoudt, "Explosives Detection: A Challenge for Physical Chemistry". *Annual Review of Physical Chemistry*, 49, 203-232, 1998.
REF. 2: N. B. Colthup, et al, "Introduction to Infrared and Raman Spectrocopy". *Academic Press*, 1990.
REF. 3: K. Kneipp, et al, "Single Molecule Detection Using Surface-Enhanced Raman Scattering". *Physical Review Letters*, 78(9), 1667-1670, 1997.
REF. 4: S. M. Nie and S. R. Emery, "Probing Single Molecules and Single Nanoparticles by Surface-Enhanced Raman Scattering". *Science*, 275(5303), 1102-1106, 1997.
REF. 5: H. X. Xu, et al, "Spectroscopy of Single Hemoglobin Molecules by Surface Enhanced Raman Scattering". *Physical Review Letters*, 83(21), 4357-4360, 1999.
REF. 6: K. Kneipp and H. Kneipp, "Surface Enhanced Raman Scattering—a Tool for Ultrasensitive Trace Analysis". *Canadian Journal of Analytical Sciences and Spectroscopy*, 48(2), 125-131, 2003.
REF. 7: K. Kneipp, et al, "Surface-Enhanced Raman Scattering and Biophysics". *Journal of Physics-Condensed Matter*, 14(18), R597-R624, 2002.
REF. 8: H. X. Xu, et al, "Electromagnetic Contributions to Single-Molecule Sensitivity in Surface-Enhanced Raman Scattering". *Physical Review E*, 62(3), 4318-4324, 2000.
REF. 9: L. D. Qin, et al, "Fabricating, and Imaging Raman Hot Spots". *Proceedings of the National Academy of Sciences of the United States of America*, 103(36), 13300-13303, 2006.
REF. 10: P. J. Schuck, et al, "Improving the Mismatch between Light and Nanoscale Objects with Gold Bowtie Nanoantennas". *Physical Review Letters*, 94(1), 017402-1-4, 2005.
REF. 11: K. H. Su, et al, "Tunable and Augmented Plasmon Resonances of Au/Sio2/Au Nanodisks". *Applied Physics Letters*, 88(6), 063118-1~3, 2006.
REF. 12: J. H. Tian, et al, "Study of Molecular Junctions with a Combined Surface-Enhanced Raman and Mechanically Controllable Break Junction Method". *Journal of the American Chemical Society*, 128(46), 14748-14749, 2006.
REF. 13: D. R. Ward, et al, "Simultaneous Measurements of Electronic Conduction and Raman Response in Molecular Junctions". *Nano Letters*, 8(3), 919-929, 2008.
REF. 14: Note that silver nanoparticles are also appropriate for the PNA technology in term of process and effect. In this description we only chose gold nanoparticles only as an example.
REF. 15: R. M. Bakker, et al, "Near-field excitation of nanoantenna resonance". *OPTICS EXPRESS*, 15(21), 13682-13688, 2007.
REF. 16: P. L. Stiles, et al, "Surface-Enhanced Raman Spectroscopy". *Annual Review of Analytical Chemistry*, 1, 601-626, 2008.
REF. 17: R. Adato, et al, "Radiative engineering of plasmon lifetimes in embedded nanoantenna arrays". *OPTICS EXPRESS*, 18(5), 4526-4537, 2010.
REF. 18: B. Yan, et al, "Engineered SERS Substrates with Multiscale Signal Enhancement: Nanoparticle Cluster Arrays". *Annual Review of Analytical Chemistry*, 1, 601-626, 2008.
REF. 19: R. H. Tredgold, "The physics of Langmuir-Blodgett films", *Rep. Prog. Phys.* 50, 1609-1656, 1987.
REF. 20: S. Chen, "Langmuir-Blodgett Fabrication of Two-Dimensional Robust Cross-Linked Nanoparticle Assemblies". *Langmuir*, 17, 2878-2884, 2001.
REF. 21: Y. Tian and J. H. Fendler, "Langmuir-Blodgett Film Formation from Fluorescence-Activated, Surfactant-Capped, Size-Selected CdS Nanoparticles Spread on Water Surfaces". *Chem. Mater.*, 8, 969-974, 1996.
REF. 22: Weixing Lu, et al., "Polymerization of 10,12-pentacosadiynoic acid monolayer at varying surface pressure and temperature". *Langmuir*, 16(6), 2791-2801, 2000.
REF. 23: R. H. Tredgold, et al., "Synthetic opals made by the Langmuir-Blodgett method". *Thin Solid Films*, 437, 276-279, 2003.

We claim:

1. A method of preparing a plasmonic nano-antennae array structure by performing the following steps:
    a. pretreating a solid substrate having a solid substrate surface with a 3-Mercaptopropyltrimethoxysilane vapor (MPS vapor) to form a self-assembling monolayer (SAM) on the solid substrate surface, the pretreating comprised of exposing the solid substrate surface to the MPS vapor followed by a dehydration process;
    b. acquiring a water-filled Langmuir-Blodgett trough system having a liquid/gas interface, at least one barrier, each barrier being movable, at least one surface pressure sensor, and a dipping device that lowers or raises the solid substrate through the liquid/gas interface that controls dipping time; the barrier movements and dipping rates being coordinated to maintain precision control over the dehydration process;
    c. preparing a plurality of capped nanoparticles by combining a plurality of nanoparticles with a plurality of capping molecules, the capping molecules being selected from the group consisting of donor ligands, linear polymer, surfactants and polyelectrolytes, and a combination thereof, and the nanoparticles being selected from the group consisting of gold (Au), Silver (Ag), Rhodium (Rh), Palladium (Pd), Osmium (Os), Iridium (Ir), Platinum (Pt), Titanium (Ti) and Aluminum (Al), and a combination thereof;
    d. spreading a monolayer of the capped nanoparticles on the liquid/gas interface;
    e. depositing the self-assembling monolayer (SAM) of the capped nanoparticles onto the solid substrate surface using the Langmuir-Blodgett trough by precisely controlling the dipping time in coordination with each surface pressure sensor and a movement of at least one barrier thereby producing a plurality of capped nanoparticles wherein the capped nanoparticles deposited on the solid substrate surface having a well-defined structure with a predetermined size, thickness and nano-gap dimensions between the capped nanoparticles;
    f. drying the solid substrate in air, the solid substrate thereby creating a strongly bonded, stable and uniform monolayer array of the capped nanoparticles.

2. The method of claim 1 wherein a 3-dimensional nano-antenna array is assembled by parallel arrangement of a plurality of 2-dimensional nano-antenna arrays and fixed with a frame.

3. A method of preparing a plasmonic nano-antennae array structure by performing the following steps:
    a. pretreating a solid substrate having a solid substrate surface with a 3-Mercaptopropyltrimethoxysilane vapor (MPS vapor) to form a self-assembling monolayer (SAM) on the solid substrate surface, the pretreating comprised of exposing the solid substrate surface to the MPS vapor followed by a dehydration process;

b. acquiring a water-filled Langmuir-Blodgett trough system having a water/air interface, at least one barrier, each barrier being movable, at least one surface pressure sensor, and a dipping device that lowers or raises the solid substrate through the water/air interface that controls dipping time; the barrier movements and dipping rates being coordinated to maintain precision control over the dehydration process;

c. preparing a plurality of capped nanoparticles by combining a plurality of nanoparticles with a plurality of capping molecules, the capping molecules being selected from the group consisting of donor ligands, linear polymer, surfactants and polyelectrolytes, and a combination thereof, and the nanoparticles being selected from the group consisting of gold (Au), Silver (Ag), Rhodium (Rh), Palladium (Pd), Osmium (Os), Iridium (Ir), Platinum (Pt), Titanium (Ti) and Aluminum (Al), and a combination thereof;

d. spreading a monolayer of the capped nanoparticles on the water/air interface;

e. depositing the self-assembling monolayer (SAM) of the capped nanoparticles onto the solid substrate surface using the Langmuir-Blodgett trough by precisely controlling the dipping time in coordination with each surface pressure sensor and a movement of at least one barrier thereby producing a plurality of capped nanoparticles wherein the capped nanoparticles deposited on the solid substrate surface having a well-defined structure with a predetermined size, thickness and nano-gap dimensions between the capped nanoparticles;

f. drying the solid substrate in air, the solid substrate thereby creating a strongly bonded, stable and uniform monolayer array of the capped nanoparticles.

4. The method of claim 3 wherein at least one additional nanoparticle layer is deposited onto the solid substrate by repeating steps c, d, e, and f for each additional nanoparticle layer deposited onto the solid substrate.

5. The method of claim 4 wherein each deposition of the additional nanoparticle layer is implemented by covering the solid substrate with a predesigned micro-precision mask thereby creating a nanoparticle matrix pattern on the solid substrate surface.

6. The method of claim 3 wherein the solid substrate is selected from the group consisting of glass, metal, plastic, acrylic, carbon fiber, optical fiber core, and a combination thereof.

7. The method of claim 3 wherein the solid substrate is a polished optical fiber core surface.

8. The method of claim 6 wherein a portion of the optical fiber core surface is polished by an annular polishing technique and then pretreated by self-assembling a thiol-terminated thin monolayer on the polished optical fiber core surface.

9. A sample collection and analysis system comprising:
a precision sensing unit that includes a 3D plasmonic nano-antenna array structure that is uniformly deposited on a surface of an optical fiber bundle;
a Raman-Scattering gas sensor system with a uniquely designed vapor sampling device; system software;
a unit comprising a laser, a Ramon spectrometer, a microcomputer and an air vacuum pump;
the database having a plurality of molecular spectrum profiles;
a wand attached to the unit, the wand having a suction head and a special head gas flow channel;
the optical fiber bundle being secured with a frame such that when one or more air samples are drawn into the suction head's gas flow, the air samples passing through the optical fiber bundle-thereby producing scattered laser light;
the scattered laser light is guided through optical lenses and filters back through optical fibers in the wand and into the unit's Ramon spectrum analyzer which produces spectrum data, the spectrum data being fed to the microcomputer, the microcomputer analyzing and comparing the plurality of molecular spectrum profiles with a spectrum of data profiles stored in memory and outputs a best match.

10. The sample collection and analysis system of claim 9 wherein the system software is controlled through a portable USB data acquisition card; the system software having a repeatable system operating sequence,
the system operating sequence including a sample suck-in period $\Delta t_s$, a sample adsorption period $\Delta t_a$, and a sample blow-out period $\Delta t_b$ such that at least one air sample is collected and analyzed.

11. The sample collection and analysis system of claim 9 wherein a predesigned micro-precision mask is designed to increase the sensitivity to a set of specific Ramon scattering laser light frequencies.

12. The sample sensing and analysis unit of claim 9 including a plasmonic nano-antennae array structure comprising a strongly bonded, stable and uniform monolayer array of capped nanoparticles bonded to a solid substrate having a solid substrate surface, the plasmonic nano-antennae array structure having a well-defined structure with a predetermined size, thickness and nano-gap dimensions between the capped nanoparticles.

13. The plasmonic nano-antennae array structure of claim 12 further comprising:
a self-assembling monolayer (SAM) deposited on the solid substrate surface;
a plurality of capped nanoparticles having at least two nanoparticles and having a plurality of capping molecules, the capping molecules being selected from the group consisting of donor ligands, linear polymer, surfactants and polyelectrolytes, and a combination thereof, and the nanoparticles being selected from the group consisting of gold (Au), Silver (Ag), Rhodium (Rh), Palladium (Pd), Osmium (Os), Iridium (Ir), Platinum (Pt), Titanium (Ti) and Aluminum (Al), and a combination thereof;
the self-assembling monolayer (SAM) of the capped nanoparticles being packed on the solid substrate surface wherein the solid substrate forming a strongly bonded, stable and uniform monolayer array of the capped nanoparticles having the well-defined structure with the predetermined size, thickness and gap dimensions between the nanoparticles.

14. The plasmonic nano-antennae array structure of claim 13 having a plurality of nanoparticle layer deposited onto the solid substrate.

15. The plasmonic nano-antennae array structure of claim 13 wherein the solid substrate is selected from the group consisting of glass, metal, acrylic, plastic, optical fiber core, textile, and a combination thereof.

16. The sample collection and analysis system of claim 9 further comprising a 3-dimensional nano-antenna array assembled by parallel arrangement of a plurality of 2-dimensional nano-antenna arrays fixed in place with a frame.

17. The plasmonic nano-antennae array structure of claim 16 wherein the solid substrate is a polished optical fiber core surface.

18. The plasmonic nano-antennae array structure of claim 17 wherein the polished optical fiber core surface has dimensions of approximately 15 mm.

* * * * *